(12) United States Patent
Goertz et al.

(10) Patent No.: US 9,770,023 B2
(45) Date of Patent: Sep. 26, 2017

(54) ACTIVE COMPOUND COMBINATIONS COMPRISING PHENYLAMIDINE COMPOUNDS AND FURTHER FUNGICIDES

(71) Applicant: BAYER CROPSCIENCE AKTIENGESELLSCHAFT, Monheim am Rhein (DE)

(72) Inventors: Andreas Goertz, Dormagen (DE); Thomas Seitz, Langenfeld (DE); Peter Dahmen, Neuss (DE); Ulrike Wachendorff-Neumann, Leuwied (DE)

(73) Assignee: BAYER CROPSCIENCE AKTIENGESELLSCHAFT, Bayer Cropscienc (DE)

( * ) Notice: Subject to any disclaimer, the term of this patent is extended or adjusted under 35 U.S.C. 154(b) by 0 days.

(21) Appl. No.: 15/117,807

(22) PCT Filed: Feb. 10, 2015

(86) PCT No.: PCT/EP2015/052710
§ 371 (c)(1),
(2) Date: Aug. 10, 2016

(87) PCT Pub. No.: WO2015/121231
PCT Pub. Date: Aug. 20, 2015

(65) Prior Publication Data
US 2017/0006868 A1 Jan. 12, 2017

(30) Foreign Application Priority Data

Feb. 13, 2014 (EP) .................................. 14154956

(51) Int. Cl.
| | | |
|---|---|---|
| *A01N 37/52* | (2006.01) | |
| *A01N 43/54* | (2006.01) | |
| *A01N 37/36* | (2006.01) | |
| *A01N 43/40* | (2006.01) | |
| *A01N 43/653* | (2006.01) | |
| *A01N 43/56* | (2006.01) | |

(52) U.S. Cl.
CPC ............ *A01N 37/52* (2013.01); *A01N 37/36* (2013.01); *A01N 43/40* (2013.01); *A01N 43/54* (2013.01); *A01N 43/56* (2013.01); *A01N 43/653* (2013.01)

(58) Field of Classification Search
CPC ........ A01N 37/52; A01N 37/36; A01N 43/40; A01N 43/54; A01N 43/56; A01N 43/653
USPC .......................................................... 514/269
See application file for complete search history.

(56) References Cited

U.S. PATENT DOCUMENTS

| 4,245,432 A | 1/1981 | Dannelly |
| 4,272,417 A | 6/1981 | Barke et al. |
| 4,808,430 A | 2/1989 | Kouno |
| 5,876,739 A | 3/1999 | Turnblad et al. |
| 2003/0176428 A1 | 9/2003 | Schneidersmann et al. |
| 2009/0018176 A1 | 1/2009 | Dahmen et al. |

FOREIGN PATENT DOCUMENTS

| WO | 00/46184 A1 | 8/2000 |
| WO | 02/28186 A2 | 4/2002 |
| WO | 02/080675 A1 | 10/2002 |
| WO | 03/024219 A1 | 3/2003 |
| WO | 2005/089547 A1 | 9/2005 |
| WO | 2005/094582 A1 | 10/2005 |
| WO | 2005/120234 A2 | 12/2005 |
| WO | 2007/031507 A1 | 3/2007 |
| WO | 2008/110313 A1 | 9/2008 |

OTHER PUBLICATIONS

Colby, S.R., "Calculating Synergistic and Antagonistic Responses of Herbicide Combinations", Weeds 1967, 15.

*Primary Examiner* — Kristin Vajda
(74) *Attorney, Agent, or Firm* — McBee Moore Woodward & Vanik IP, LLC; Susan McBee; David Woodward

(57) ABSTRACT

The present invention relates to novel fungicidal active compound combinations or compositions comprising a phenylamidine compound of formula (I) and further active compounds (II) and (III) selected from the groups (A), (B) and/or (C), to a process for preparing these active compound combinations or compositions and to the use thereof as biologically active compound combinations or compositions, especially for the control of phytopathogenic fungi in plants and/or in the protection of materials and/or as plant growth regulators.

18 Claims, No Drawings

ACTIVE COMPOUND COMBINATIONS COMPRISING PHENYLAMIDINE COMPOUNDS AND FURTHER FUNGICIDES

CROSS REFERENCE TO RELATED APPLICATIONS

This application is a §371 National State Application of PCT/EP2015/052710, filed Feb. 10, 2015, which claims priority to European Application No. 14154956.8 filed Feb. 13, 2014.

BACKGROUND

Field of Invention

The present invention relates to novel fungicidal active compound combinations comprising a phenylamidine compound of formula (I) and further active compounds (II) and (III), selected from the groups (A), (B) and/or (C) to a process for preparing these active compound combinations and to the use thereof as biologically active compound combinations or crop protection compositions, especially for the control of phytopathogenic fungi in plants and/or in the protection of materials and/or as plant growth regulators.

Description of Related Art

WO-A 00/46 184 and WO-A 08/110313 each disclose the use of phenylamidines as fungicides and their preparation starting from commercially available materials. WO-A 08/110313 discloses phenoxyphenyl-amidine compounds according to formula (I), methods for producing such compounds starting from commercially available ingredients and their fungicidal uses.

WO-A 03/024 219, WO-A 05/089 547 and WO-A 05/120 234 generally disclose fungicide compositions comprising at least one phenylamidine and at least one further known fungicidally active ingredient. Object of these earlier inventions are mainly binary compositions referring inter alia to the binary combination of phenylamidines and further fungicides. Further it is generally stated therein, that such binary compositions may further comprise additional components such as fungicides but no concrete ternary combinations are specified.

Since the environmental and economic requirements imposed on modern-day crop protection compositions are continually increasing, with regard, for example, to the spectrum of action, toxicity, selectivity, application rate, formation of residues, and favourable preparation ability, and since, furthermore, there may be problems, for example, with resistances, a constant task is to develop new, alternative crop protection compositions, in particular fungicidal crop protection compositions, which in some areas at least help to fulfil the abovementioned requirements. One way of fulfilling such need can be the development of novel compositions comprising several fungicides which have advantages over the known compositions at least in some areas.

In view of this, it was in particular an object of the present invention to provide active compound combinations or compositions which exhibit fungicidal activity against phytopathogenic fungi in plants, in the protection of materials and as plant growth regulators. Moreover, it was a further particular object of the present invention, to reduce the application rates and broaden the activity spectrum of the fungicides, and thereby to provide an active compound combination or composition which, preferably at a reduced total amount of active compounds applied, has improved fungicidal activity against phytopathogenic fungi.

The present invention provides active compound combinations or compositions which in some aspects at least achieve the stated objective, i.e. which exhibit fungicidal activity against phytopathogenic fungi in plants and/or in the protection of materials and/or as plant growth regulators. Moreover it has been found, surprisingly, that the active compound combinations according to the invention not only bring about the additive enhancement of the spectrum of action with respect to the phytopathogenic fungi to be controlled that was in principle to be expected but achieves a synergistic effect which extends the range of action of the component (I) and of the components (II) and (III) in two ways. Firstly, the rates of application of the component according to formula (I) and of the components (II) and (III) are lowered whilst the action remains equally good. Secondly, the active compound combination still achieves a high degree of control of phytopathogenic fungi in plants even where the three individual compounds have become totally ineffective in such a low application rate range. This allows, on the one hand, a substantial broadening of the spectrum of phytopathogenic fungi that can be controlled and, on the other hand, increased safety in use.

In addition to the fungicidal synergistic activity, the active compound combinations according to the invention have further surprising properties which, in a wider sense, may also be called synergistic, such as, for example: broadening of the fungicidal activity spectrum to resistant strains of plant diseases, such as fungicide resistant phytopathogenic fungi; lower application rates of the active compound combinations; sufficient control of phytopathogenic fungi with the aid of the active compound combinations according to the invention even at application rates where the individual compounds show no or virtually no activity; advantageous behaviour during formulation or during use; improved storage stability and light stability; advantageous residue formation; improved toxicological or ecotoxicological behaviour; improved properties of the plant so called plant physiology effects, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young plants stand healthy, which, for example, safeguards quality and yield. Moreover, the active compound combinations according to the invention may contribute to enhanced systemic action. Even if the individual compounds of the active compound combination have no sufficient systemic properties, the active compound combinations according to the invention may have this property. In a similar manner, the active compound combinations according to the invention may result in higher long term efficacy of the fungicidal action.

SUMMARY OF THE INVENTION

It has surprisingly been found that active compound combinations comprising (1) at least one compound of the formula (I)

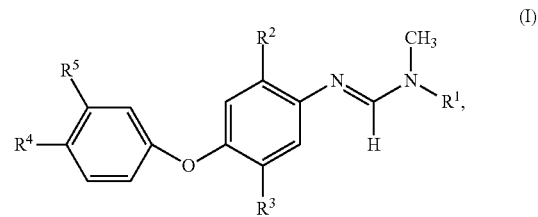

in which
- R¹ is selected from the group consisting of methyl and ethyl;
- R² is selected from the group consisting of a Cl atom and a methyl group;
- R³ is selected from the group consisting of a Cl-atom and a methyl group;
- R⁴ is selected from the group consisting of hydrogen, halogen or methyl;
- R⁵ is selected from the group consisting of hydrogen, halogen or methyl;

and salts, N-oxides, metal complexes or stereoisomers thereof
and
(2) at least two compounds (II) and (III) selected from the groups (A), (B) and/or (C):
   (A) the group of inhibitors of the ergosterol biosynthesis;
   (B) the group of inhibitors of the respiratory chain at complex I or II; and
   (C) the group of inhibitors of the respiratory chain at complex III;
   with the proviso that the specified compounds (II) and (III) are not identical;

act in a fungicidal fashion. Accordingly, the present invention is directed to ternary active compound combinations of compounds of the formula (I) and compounds (II) and (III) selected from the groups (A), (B) and/or (C). In some embodiments, such active compound combinations or compositions act in a synergistic fashion.

In case a compound of the group (A) is used in combination with the compound of the formula (I) and a further active compound, the compound (A) of the group of inhibitors of the ergosterol biosynthesis is selected from the group consisting of (A.1) cyproconazole (113096-99-4), (A.2) epoxiconazole (106325-08-0), (A.3) prothioconazole (178928-70-6) and/or (A.4) tebuconazole (107534-96-3).

In case a compound of the group (B) is used in combination with the compound of the formula (I) and a further active compound, the compound (B) of the group of inhibitors of the respiratory chain at complex I or II is selected from the group consisting of (B.1) bixafen (581809-46-3), (B.2) fluopyram (658066-35-4), (B.3) fluxapyroxad (907204-31-3), (B.4) isopyrazam (mixture of syn-epimeric racemate 1RS,4SR,9RS and anti-epimeric racemate 1RS,4SR,9SR) (881685-58-1), (B.5) penthiopyrad (183675-82-3), (B.6) benzovindiflupyr (1072957-71-1), (B.7) isofetamid (875915-78-9), (B.8) N-(5-chloro-2-isopropylbenzyl)-N-cyclopropyl-3-(difluoromethyl)-5-fluoro-1-methyl-1H-pyrazole-4-carboxamide and/or (B.9) 3-(difluoromethyl)-N-methoxy-1-methyl-N-[1-(2,4,6-trichlorophenyl)propan-2-yl]-1H-pyrazole-4-carboxamide.

In case a compound of the group (C) is used in combination with the compound of the formula (I) and a further active compound, the compound (C) of the group of inhibitors of the respiratory chain at complex III is selected from the group consisting of (C.1) azoxystrobin (131860-33-8), (C.2) picoxystrobin (117428-22-5), (C.3) pyraclostrobin (175013-18-0) and/or (C.4) trifloxystrobin (141517-21-7).

The invention also comprises a composition comprising an active compound combination according to the invention. Such a composition can further comprise at least one agriculturally suitable additive. The invention also comprises a method for preparing compositions comprising adding at least one agriculturally suitable additive to the active compound combination according to the invention. Furthermore the invention comprises a method for reducing damage of plants and plant parts or losses in harvested fruits or vegetables caused by phytopathogenic fungi by controlling such phytopathogenic fungi, comprising applying the active compound combination or the crop protection composition to the plant or the phytopathogenic fungi or the habitat of the plant or the habitat of the phytopathogenic fungi. Furthermore the invention encompasses a method for curatively or preventively controlling phytopathogenic fungi comprising the use of an active compound combination or a composition for control of soybean diseases. Furthermore the invention encompasses a method for curatively or preventively controlling phytopathogenic fungi comprising the use of an active compound combination or a composition for control of cereal diseases. The invention also encompasses the use of the active compound combination or the crop protection composition for reducing damage of plants and plant parts or losses in harvested fruits or vegetables caused by phytopathogenic fungi by controlling such phytopathogenic fungi. In this connection the plants can be genetically modified or non-genetically modified. Furthermore the invention comprises the use of active compound combinations or compositions according to the invention for the treatment of seed, comprising contacting said seeds with the active compound combinations or compositions. Finally, the present invention also relates to seed treated with the above-mentioned active compound combination or crop protection composition.

In view of this, the problem underlying the present invention has been solved by providing novel active compound combinations or crop protection compositions which exhibit synergistic fungicidal activity against phytopathogenic fungi in plants. Moreover, the novel active compound combinations or crop protection compositions according to the invention enable reduced application rates and/or broaden the activity spectrum of the fungicides. Finally the novel active compound combinations or crop protection compositions provide improved fungicidal activity against phytopathogenic fungi and consequently provide efficient disease control for reducing damage of plants and plant parts or losses in harvested fruits or vegetables.

DETAILED DESCRIPTION OF A PREFERRED EMBODIMENT

The present invention provides active compound combinations comprising at least one compound of the formula (I) and at least two further active compounds (II) and (III) as outlined above. Accordingly, the present invention is directed to ternary active compound combinations of the compounds of the formula (I) and compounds (II) and (III).

According to the invention the term "active compound combination" shall mean a physical mixture comprising compounds of the formula (I) and compounds (II) and (III) selected from the groups (A), (B) and/or (C). In the context of the present invention the expression "active compound combination" stands for the various combinations of compounds (I), (II) and (III), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (I), (II) and (III) is not essential for working the present invention. According to the invention the term "composition" means a combination of the active compound combination with further agriculturally suitable additives, such as agriculturally suitable auxiliaries, e.g. solvents, carriers, surfactants, extenders or the like which are described later. The term "composition" also comprises the terms "crop protection composition" and "formulation".

In general "pesticides" as well as the terms "pesticidal" and "acting in a pesticidal fashion" means the ability of a substance to exhibit activity against harmful microorganisms and plant pests e.g. increase mortality or inhibit the growth rate of harmful microorganisms and/or plant pests. According to the present invention the term "harmful microorganisms" includes phytopathogenic fungi and bacteria, in a preferred embodiment it refers to phytopathogenic fungi. Furthermore in the sense of the present invention the term "plant pests" include insects and/or nematodes.

"Fungicides" as well as the terms "fungicidal", "fungicidal activity" and "acting in a fungicidal fashion" refer to the ability of a substance to increase mortality or inhibit growth rates of phytopathogenic fungi. Fungicides can be used in crop protection for control of phytopathogenic fungi. They are characterized by an outstanding efficacy against a broad spectrum of phytopathogenic fungi. As used herein, the term "phytopathogenic fungi" comprises all organisms of the kingdom of fungi including Oomycetes, which can cause damage of plants and/or damage of plant parts and/or losses in harvested fruits or vegetables. Specific phytopathogenic fungi are described later.

"Insecticides" as well as the term "insecticidal" refers to the ability of a substance to increase mortality or inhibit growth rate of insects. As used herein, the term "insects" comprises all organisms in the class "Insecta".

"Nematicide" and "nematicidal" refers to the ability of a substance to increase mortality or inhibit the growth rate of nematodes. In general, the term "nematode" comprises eggs, larvae, juvenile and mature forms of said organism.

In the context of the present invention the term "damage of plants" or "damage of plant parts" comprises in comparison to uninfected or unharmed plants e.g. the decrease of plant growth or yield or the decrease of plant vigor, comprising decrease of plant health, plant quality and seed vigor, a decreased resistance to harmful microorganisms such as phytopathogenic fungi, a decreased abiotic stress tolerance, comprising decreased temperature tolerance, decreases drought tolerance and decreased recovery after drought stress, decreased water use efficiency (correlating to reduced water consumption), decreases flood tolerance, decreased ozone stress and UV tolerance, decreased tolerance towards chemicals like heavy metals, salts, pesticides (safener) or the like, an increased stand failure, decreased recovery, impaired greening effect and decreased photosynthetic efficiency. In particular such damages of plants or damage of plant parts are caused by phytopathogenic fungi.

Reducing the damage of plants and plant parts often results in healthier plants and/or in an increase in plant vigor and yield. The active compound combinations and/or compositions according to the invention, in combination with good plant tolerance and favourable toxicity to warm-blooded animals and being tolerated well by the environment, are suitable for protecting plants and plant parts, for increasing harvest yields and for improving the quality of the harvested material.

In the context of the present invention, "control of harmful microorganisms" or "control of phytopathogenic fungi" means a reduction in infestation by harmful microorganisms, especially of phytopathogenic fungi, compared with the untreated plant measured as pesticidal efficacy, preferably a reduction by 25-50%, compared with the untreated plant (100%), more preferably a reduction by 40-79%, compared with the untreated plant (100%); even more preferably, the infection by harmful microorganisms especially of phytopathogenic fungi is entirely suppressed (by 70-100%). In a specific embodiment the active compound combinations and/or compositions according to the invention can be used for curative (i.e. for treatment of already infected plants) or protective or preventive (i.e. for treatment of plants which have not yet been infected) control of phytopathogenic fungi. The invention therefore also relates to curative and protective methods for controlling phytopathogenic fungi by the use of the inventive active compound combinations and/or compositions. The active compound combinations and/or compositions according to the invention are active against normally sensitive and resistant species of phytopathogenic fungi and against all or some stages of development. The term "preventive control of phytopathogenic fungi" comprises the use of active compound combinations and/or compositions according to the invention for the prevention of plant diseases. Thus, a further aspect of the present invention is the use of active compound combinations and/or compositions according to the invention for controlling phytopathogenic fungi, e.g., in agriculture, in horticulture, in forests, in gardens and leisure facilities as well as in the protection of stored products and materials.

The term "applying the composition to the plant or the phytopathogenic fungi or the habitat of the plant or the habitat of the phytopathogenic fungi" refers to the treatment of a plant and/or phytopathogenic fungi and/or the habitat of the plant or the phytopathogenic fungi with the compositions according to the invention. The term "habitat of the plant" comprises the environment where the plant is growing, e.g. the soil or nutrition medium—which is in a radius of at least 30 cm, 20 cm, 10 cm around the caulis or bole of a plant to be treated or which is at least 30 cm, 20 cm, 10 cm around the root system of said plant to be treated, respectively. The term "habitat of the phytopathogenic fungi" as used herein is defined as the seed, the plant or plant parts or the fruit. It also comprises the soil or the nutrition medium in which the plant grows—which is in a radius of at least 30 cm, 20 cm, 10 cm around the caulis or bole of a plant to be treated or which is at least 30 cm, 20 cm, 10 cm around the root system of said plant to be treated, respectively.

As used herein, the term "comprising" is to be interpreted as specifying the presence of the stated features, integers, steps, components or compounds as referred to, but does not preclude the presence or addition of one or more features, integers, steps, components or compounds, or groups thereof. Thus, e.g. an active compound combination or composition comprising a compound of the formula (I) and at least compounds (II) and (III) selected from the groups (A), (B) and/or (C) may comprise more compounds than the actually cited ones, i.e. the active compound combination or composition may further comprise at least one further feature, integer, step, component or compound, or groups thereof. However, in context with the present invention, the term "comprising" also encloses "consisting of" and "including".

As used herein the term "at least one" shall refer to either one compound, feature, integer, step, component or compound, but also encompasses the presence of (at least) two, (at least) three or (at least) four features, integers, steps, components or compounds, or groups thereof.

In the following preferred active compound combinations comprising compounds of the general formula (I) and compounds selected from the groups (A), (B) and/or (C) are described.

In a first preferred embodiment of the present invention, the compound of the general formula (I) is combined with at least one member of (A) the group of inhibitors of the ergosterol biosynthesis and at least one member of (B) the group of inhibitors of the respiratory chain at complex I or II.

In a second preferred embodiment of the present invention, the compound of the general formula (I) is combined with at least one member of (A) the group of inhibitors of the ergosterol biosynthesis and at least one member of (C) the group of inhibitors of the respiratory chain at complex III.

In a third preferred embodiment of the present invention, the compound of the general formula (I) is combined with at least one member of (B) the group of inhibitors of the respiratory chain at complex I or II and at least one member of (C) the group of inhibitors of the respiratory chain at complex III.

In a fourth preferred embodiment of the present invention, the compound of the general formula (I) is combined with at least two members of (A) the group of inhibitors of the ergosterol biosynthesis.

In a fifth preferred embodiment of the present invention, the compound of the general formula (I) is combined with at least two members of (B) the group of inhibitors of the respiratory chain at complex I or II.

In a sixth preferred embodiment of the present invention, the compound of the general formula (I) is combined with at least two members of (C) the group of inhibitors of the respiratory chain at complex III.

Preferred active compound combinations are the following combinations selected from the group consisting of: (I)+(B.1)+(A.3); (I)+(B.2)+(A.3); (I)+(B.6)+(A.3); (I)+(C.4)+(A.3); (I)+(C.1)+(A.3); (I)+(B.8)+(A.3); (I)+(B.1)+(A.4); (I)+(C.4)+(A.4); (I)+(B.8)+(A.4); (I)+(C.4)+(B.1); (I)+(C.1)+(B.6); (I)+(C.2)+(B.5); (I)+(C.2)+(B.6); (I)+(C.3)+(B.3); (I)+(B.8)+(C.4); (I)+(B.2)+(A.4); (I)+(C.4)+(A.1); (I)+(B.7)+(A.3); (I)+(B.7)+(A.4); (I)+(C.4)+(A.1); (I)+(B.2)+(B.1); (I)+(C.4)+(B.2); (I)+(B.7)+(B.1); (I)+(B.7)+(C.4); (I)+(B.6)+(A.4); (I)+(B.6)+(A.1); (I)+(B.6)+(A.2); (I)+(B.5)+(A.1); (I)+(B.5)+(A.2); (I)+(B.3)+(A.3); (I)+(B.3)+(A.4); (I)+(B.3)+(A.2); (I)+(B.4)+(A.1); (I)+(B.4)+(A.2); (I)+(C.4)+(B.6); (I)+(C.4)+(B.3); (I)+(C.1)+(A.4); (I)+(C.1)+(A.1); (I)+(C.1)+(A.2); (I)+(C.1)+(B.1); (I)+(C.1)+(B.3); (I)+(C.1)+(B.4); (I)+(C.3)+(A.3); (I)+(C.3)+(A.4); (I)+(C.3)+(A.2); (I)+(C.3)+(B.1); (I)+(C.2)+(A.3); (I)+(C.2)+(A.4); (I)+(B.8)+(C.1); (I)+(B.8)+(C.3); (I)+(B.9)+(A.4); (I)+(B.9)+(B.1) and (I)+(B.9)+(B.6).

Particularly preferred active compound combinations are the following combinations selected from the group consisting of: (I)+(B.6)+(A.4); (I)+(B.6)+(A.1); (I)+(B.6)+(A.2); (I)+(B.5)+(A.1); (I)+(B.5)+(A.2); (I)+(B.3)+(A.3); (I)+(B.3)+(A.4); (I)+(B.3)+(A.2); (I)+(B.4)+(A.1); (I)+(B.4)+(A.2); (I)+(C.4)+(B.6); (I)+(C.4)+(B.3); (I)+(C.1)+(A.4); (I)+(C.1)+(A.1); (I)+(C.1)+(A.2); (I)+(C.1)+(B.1); (I)+(C.1)+(B.3); (I)+(C.1)+(B.4); (I)+(C.3)+(A.3); (I)+(C.3)+(A.4); (I)+(C.3)+(A.2); (I)+(C.3)+(B.1); (I)+(C.2)+(A.3); (I)+(C.2)+(A.4); (I)+(B.8)+(C.1); (I)+(B.8)+(C.3); (I)+(B.9)+(A.4); (I)+(B.9)+(B.1) and (I)+(B.9)+(B.6).

More preferred active compound combinations are the following combinations selected from the group consisting of: (I)+(B.2)+(A.4); (I)+(C.4)+(A.1); (I)+(B.7)+(A.3); (I)+(B.7)+(A.4); (I)+(C.4)+(A.1); (I)+(B.2)+(B.1); (I)+(C.4)+(B.2); (I)+(B.7)+(B.1) and (I)+(B.7)+(C.4).

Most preferred active compound combinations are the following combinations selected from the group consisting of: (I)+(B.1)+(A.3); (I)+(B.2)+(A.3); (I)+(B.6)+(A.3); (I)+(C.4)+(A.3); (I)+(C.1)+(A.3); (I)+(B.8)+(A.3); (I)+(B.1)+(A.4); (I)+(C.4)+(A.4); (I)+(B.8)+(A.4); (I)+(C.4)+(B.1); (I)+(C.1)+(B.6); (I)+(C.2)+(B.5); (I)+(C.2)+(B.6); (I)+(C.3)+(B.3) and (I)+(B.8)+(C.4).

In a preferred embodiment of the present invention the active compound combinations comprise compounds of the formula (I) wherein the phenylamidine derivatives are represented by the following formula (I-a):

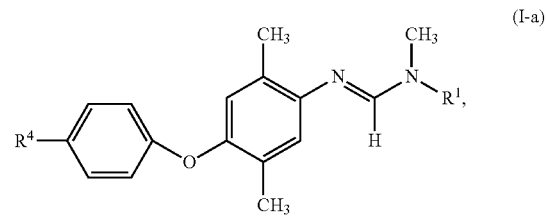

in which
R¹ is selected from the group consisting of methyl and ethyl;
R⁴ is selected from the group consisting of hydrogen, bromine, chlorine, fluorine or methyl;

and salts, N-oxides, metal complexes or stereoisomers thereof and at least two compounds (II) and (III) selected from the group consisting of (A), (B) and/or (C) as mentioned above with the proviso that the specified compounds (II) and (III) are not identical.

In a particularly preferred embodiment of the present invention the active compound combinations comprise compounds of the formula (I) wherein the phenylamidine derivatives are represented by the following formula (I-b):

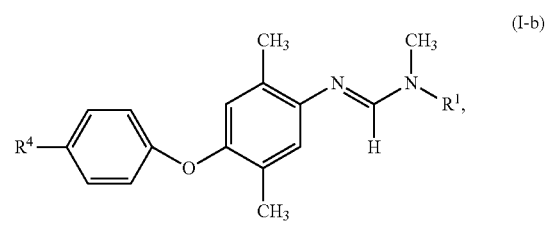

in which
R¹ is selected from the group consisting of methyl and ethyl;
R⁴ is selected from the group consisting of hydrogen, fluorine or chlorine;

and salts, N-oxides, metal complexes or stereoisomers thereof and at least two compounds (II) and (III) selected from the group consisting of (A), (B) and/or (C) as mentioned above with the proviso that the specified compounds (II) and (III) are not identical.

In a more preferred embodiment of the present invention the active compound combinations comprise compounds of the formula (I) wherein the phenylamidine derivatives are represented by the following formula (I-c):

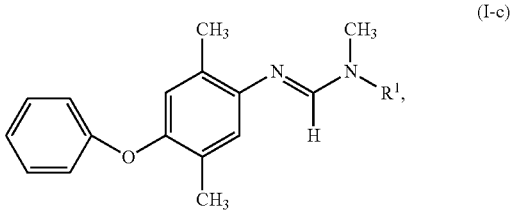

(I-c)

in which
R¹ is selected from the group consisting of methyl and ethyl;
and salts, N-oxides, metal complexes or stereoisomers thereof and at least two compounds (II) and (III) selected from the group consisting of (A), (B) and/or (C) as mentioned above with the proviso that the specified compounds (II) and (III) are not identical.

In a most preferred embodiment of the present invention the active compound combinations comprise compounds of the formula (I) wherein the phenylamidine derivatives are represented by the following formula (I-d):

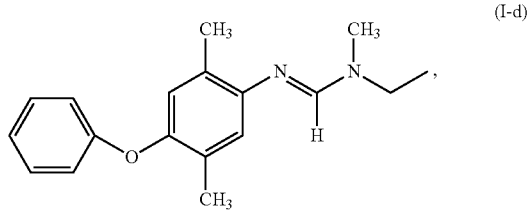 [SMILES: CCN(C)/C=N/c1cc(C)c(Oc2ccccc2)cc1C]

(I-d)

and salts, N-oxides, metal complexes or stereoisomers thereof and at least two compounds (II) and (III) selected from the group consisting of (A), (B) and/or (C) as mentioned above with the proviso that the specified compounds (II) and (III) are not identical.

In the following active compound combinations comprising compounds of the general formula (I-a) and compounds selected from the group consisting of (A), (B) and/or (C) are described.

In a first embodiment of the present invention, the compound of the general formula (I-a) is combined with at least one member of (A) the group of inhibitors of the ergosterol biosynthesis and at least one member of (B) the group of inhibitors of the respiratory chain at complex I or II.

In a second embodiment of the present invention, the compound of the general formula (I-a) is combined with at least one member of (A) the group of inhibitors of the ergosterol biosynthesis and at least one member of (C) the group of inhibitors of the respiratory chain at complex III.

In a third embodiment of the present invention, the compound of the general formula (I-a) is combined with at least one member of (B) the group of inhibitors of the respiratory chain at complex I or II and at least one member of (C) the group of inhibitors of the respiratory chain at complex III.

In a fourth embodiment of the present invention, the compound of the general formula (I-a) is combined with at least two distinct members of (A) the group of inhibitors of the ergosterol biosynthesis.

In a fifth embodiment of the present invention, the compound of the general formula (I-a) is combined with at least two distinct members of (B) the group of inhibitors of the respiratory chain at complex I or II.

In a sixth embodiment of the present invention, the compound of the general formula (I-a) is combined with at least two distinct members of (C) the group of inhibitors of the respiratory chain at complex III.

Preferred active compound combinations are the following combinations selected from the group consisting of:
(I-a)+(B.1)+(A.3); (I-a)+(B.2)+(A.3); (I-a)+(B.6)+(A.3);
(I-a)+(C.4)+(A.3); (I-a)+(C.1)+(A.3); (I-a)+(B.8)+(A.3);
(I-a)+(B.1)+(A.4); (I-a)+(C.4)+(A.4); (I-a)+(B.8)+(A.4);
(I-a)+(C.4)+(B.1); (I-a)+(C.1)+(B.6); (I-a)+(C.2)+(B.5);
(I-a)+(C.2)+(B.6); (I-a)+(C.3)+(B.3); (I-a)+(B.8)+(C.4);
(I-a)+(B.2)+(A.4); (I-a)+(C.4)+(A.1); (I-a)+(B.7)+(A.3);
(I-a)+(B.7)+(A.4); (I-a)+(C.4)+(A.1); (I-a)+(B.2)+(B.1);
(I-a)+(C.4)+(B.2); (I-a)+(B.7)+(B.1); (I-a)+(B.7)+(C.4);
(I-a)+(B.6)+(A.4); (I-a)+(B.6)+(A.1); (I-a)+(B.6)+(A.2);
(I-a)+(B.5)+(A.1); (I-a)+(B.5)+(A.2); (I-a)+(B.3)+(A.3);
(I-a)+(B.3)+(A.4); (I-a)+(B.3)+(A.2); (I-a)+(B.4)+(A.1);
(I-a)+(B.4)+(A.2); (I-a)+(C.4)+(B.6); (I-a)+(C.4)+(B.3);
(I-a)+(C.1)+(A.4); (I-a)+(C.1)+(A.1); (I-a)+(C.1)+(A.2);
(I-a)+(C.1)+(B.1); (I-a)+(C.1)+(B.3); (I-a)+(C.1)+(B.4);
(I-a)+(C.3)+(A.3); (I-a)+(C.3)+(A.4); (I-a)+(C.3)+(A.2);
(I-a)+(C.3)+(B.1); (I-a)+(C.2)+(A.3); (I-a)+(C.2)+(A.4);
(I-a)+(B.8)+(C.1); (I-a)+(B.8)+(C.3); (I-a)+(B.9)+(A.4);
(I-a)+(B.9)+(B.1) and (I-a)+(B.9)+(B.6).

Particularly preferred active compound combinations are the following combinations selected from the group consisting of: (I-a)+(B.6)+(A.4); (I-a)+(B.6)+(A.1); (I-a)+(B.6)+(A.2); (I-a)+(B.5)+(A.1); (I-a)+(B.5)+(A.2); (I-a)+(B.3)+(A.3); (I-a)+(B.3)+(A.4); (I-a)+(B.3)+(A.2); (I-a)+(B.4)+(A.1); (I-a)+(B.4)+(A.2); (I-a)+(C.4)+(B.6); (I-a)+(C.4)+(B.3); (I-a)+(C.1)+(A.4); (I-a)+(C.1)+(A.1); (I-a)+(C.1)+(A.2); (I-a)+(C.1)+(B.1); (I-a)+(C.1)+(B.3); (I-a)+(C.1)+(B.4); (I-a)+(C.3)+(A.3); (I-a)+(C.3)+(A.4); (I-a)+(C.3)+(A.2); (I-a)+(C.3)+(B.1); (I-a)+(C.2)+(A.3); (I-a)+(C.2)+(A.4); (I-a)+(B.8)+(C.1); (I-a)+(B.8)+(C.3); (I-a)+(B.9)+(A.4); (I-a)+(B.9)+(B.1) and (I-a)+(B.9)+(B.6).

More preferred active compound combinations are the following combinations selected from the group consisting of: (I-a)+(B.2)+(A.4); (I-a)+(C.4)+(A.1); (I-a)+(B.7)+(A.3); (I-a)+(B.7)+(A.4); (I-a)+(C.4)+(A.1); (I-a)+(B.2)+(B.1); (I-a)+(C.4)+(B.2); (I-a)+(B.7)+(B.1) and (I-a)+(B.7)+(C.4).

Most preferred active compound combinations are the following combinations selected from the group consisting of: (I-a)+(B.1)+(A.3); (I-a)+(B.2)+(A.3); (I-a)+(B.6)+(A.3); (I-a)+(C.4)+(A.3); (I-a)+(C.1)+(A.3); (I-a)+(B.8)+(A.3); (I-a)+(B.1)+(A.4); (I-a)+(C.4)+(A.4); (I-a)+(B.8)+(A.4); (I-a)+(C.4)+(B.1); (I-a)+(C.1)+(B.6); (I-a)+(C.2)+(B.5); (I-a)+(C.2)+(B.6); (I-a)+(C.3)+(B.3) and (I-a)+(B.8)+(C.4).

In the following further active compound combinations comprising compounds of the general formula (I-b) and compounds selected from the group consisting of (A), (B) and/or (C) are described.

In a first embodiment of the present invention, the compound of the general formula (I-b) is combined with at least one member of (A) the group of inhibitors of the ergosterol biosynthesis and at least one member of (B) the group of inhibitors of the respiratory chain at complex I or II.

In a second embodiment of the present invention, the compound of the general formula (I-b) is combined with at least one member of (A) the group of inhibitors of the ergosterol biosynthesis and at least one member of (C) the group of inhibitors of the respiratory chain at complex III.

In a third embodiment of the present invention, the compound of the general formula (I-b) is combined with at least one member of (B) the group of inhibitors of the respiratory chain at complex I or II and at least one member of (C) the group of inhibitors of the respiratory chain at complex III.

In a fourth embodiment of the present invention, the compound of the general formula (I-b) is combined with at least two distinct members of (A) the group of inhibitors of the ergosterol biosynthesis.

In a fifth embodiment of the present invention, the compound of the general formula (I-b) is combined with at least two distinct members of (B) the group of inhibitors of the respiratory chain at complex I or II.

In a sixth embodiment of the present invention, the compound of the general formula (I-b) is combined with at least two distinct members of (C) the group of inhibitors of the respiratory chain at complex III.

Preferred active compound combinations are the following combinations selected from the group consisting of: (I-b)+(B.1)+(A.3); (I-b)+(B.2)+(A.3); (I-b)+(B.6)+(A.3); (I-b)+(C.4)+(A.3); (I-b)+(C.1)+(A.3); (I-b)+(B.8)+(A.3); (I-b)+(B.1)+(A.4); (I-b)+(C.4)+(A.4); (I-b)+(B.8)+(A.4); (I-b)+(C.4)+(B.1); (I-b)+(C.1)+(B.6); (I-b)+(C.2)+(B.5); (I-b)+(C.2)+(B.6); (I-b)+(C.3)+(B.3); (I-b)+(B.8)+(C.4); (I-b)+(B.2)+(A.4); (I-b)+(C.4)+(A.1); (I-b)+(B.7)+(A.3); (I-b)+(B.7)+(A.4); (I-b)+(C.4)+(A.1); (I-b)+(B.2)+(B.1); (I-b)+(C.4)+(B.2); (I-b)+(B.7)+(B.1); (I-b)+(B.7)+(C.4); (I-b)+(B.6)+(A.4); (I-b)+(B.6)+(A.1); (I-b)+(B.6)+(A.2); (I-b)+(B.5)+(A.1); (I-b)+(B.5)+(A.2); (I-b)+(B.3)+(A.3); (I-b)+(B.3)+(A.4); (I-b)+(B.3)+(A.2); (I-b)+(B.4)+(A.1); (I-b)+(B.4)+(A.2); (I-b)+(C.4)+(B.6); (I-b)+(C.4)+(B.3); (I-b)+(C.1)+(A.4); (I-b)+(C.1)+(A.1); (I-b)+(C.1)+(A.2); (I-b)+(C.1)+(B.1); (I-b)+(C.1)+(B.3); (I-b)+(C.1)+(B.4); (I-b)+(C.3)+(A.3); (I-b)+(C.3)+(A.4); (I-b)+(C.3)+(A.2); (I-b)+(C.3)+(B.1); (I-b)+(C.2)+(A.3); (I-b)+(C.2)+(A.4); (I-b)+(B.8)+(C.1); (I-b)+(B.8)+(C.3); (I-b)+(B.9)+(A.4); (I-b)+(B.9)+(B.1) and (I-b)+(B.9)+(B.6).

Particularly preferred active compound combinations are the following combinations selected from the group consisting of: (I-b)+(B.6)+(A.4); (I-b)+(B.6)+(A.1); (I-b)+(B.6)+(A.2); (I-b)+(B.5)+(A.1); (I-b)+(B.5)+(A.2); (I-b)+(B.3)+(A.3); (I-b)+(B.3)+(A.4); (I-b)+(B.3)+(A.2); (I-b)+(B.4)+(A.1); (I-b)+(B.4)+(A.2); (I-b)+(C.4)+(B.6); (I-b)+(C.4)+(B.3); (I-b)+(C.1)+(A.4); (I-b)+(C.1)+(A.1); (I-b)+(C.1)+(A.2); (I-b)+(C.1)+(B.1); (I-b)+(C.1)+(B.3); (I-b)+(C.1)+(B.4); (I-b)+(C.3)+(A.3); (I-b)+(C.3)+(A.4); (I-b)+(C.3)+(A.2); (I-b)+(C.3)+(B.1); (I-b)+(C.2)+(A.3); (I-b)+(C.2)+(A.4); (I-b)+(B.8)+(C.1); (I-b)+(B.8)+(C.3); (I-b)+(B.9)+(A.4); (I-b)+(B.9)+(B.1) and (I-b)+(B.9)+(B.6).

More preferred active compound combinations are the following combinations selected from the group consisting of: (I-b)+(B.2)+(A.4); (I-b)+(C.4)+(A.1); (I-b)+(B.7)+(A.3); (I-b)+(B.7)+(A.4); (I-b)+(C.4)+(A.1); (I-b)+(B.2)+(B.1); (I-b)+(C.4)+(B.2); (I-b)+(B.7)+(B.1) and (I-b)+(B.7)+(C.4).

Most preferred active compound combinations are the following combinations selected from the group consisting of: (I-b)+(B.1)+(A.3); (I-b)+(B.2)+(A.3); (I-b)+(B.6)+(A.3); (I-b)+(C.4)+(A.3); (I-b)+(C.1)+(A.3); (I-b)+(B.8)+(A.3); (I-b)+(B.1)+(A.4); (I-b)+(C.4)+(A.4); (I-b)+(B.8)+(A.4); (I-b)+(C.4)+(B.1); (I-b)+(C.1)+(B.6); (I-b)+(C.2)+(B.5); (I-b)+(C.2)+(B.6); (I-b)+(C.3)+(B.3) and (I-b)+(B.8)+(C.4).

In the following further active compound combinations comprising compounds of the general formula (I-c) and compounds selected from the group consisting of (A), (B) and/or (C) are described.

In a first embodiment of the present invention, the compound of the general formula (I-c) is combined with at least one member of (A) the group of inhibitors of the ergosterol biosynthesis and at least one member of (B) the group of inhibitors of the respiratory chain at complex I or II.

In a second embodiment of the present invention, the compound of the general formula (I-c) is combined with at least one member of (A) the group of inhibitors of the ergosterol biosynthesis and at least one member of (C) the group of inhibitors of the respiratory chain at complex III.

In a third embodiment of the present invention, the compound of the general formula (I-c) is combined with at least one member of (B) the group of inhibitors of the respiratory chain at complex I or II and at least one member of (C) the group of inhibitors of the respiratory chain at complex III.

In a fourth embodiment of the present invention, the compound of the general formula (I-c) is combined with at least two members of (A) the group of inhibitors of the ergosterol biosynthesis.

In a fifth embodiment of the present invention, the compound of the general formula (I-c) is combined with at least two members of (B) the group of inhibitors of the respiratory chain at complex I or II.

In a sixth embodiment of the present invention, the compound of the general formula (I-c) is combined with at least two members of (C) the group of inhibitors of the respiratory chain at complex III.

Preferred active compound combinations are the following combinations selected from the group consisting of: (I-c)+(B.1)+(A.3); (I-c)+(B.2)+(A.3); (I-c)+(B.6)+(A.3); (I-c)+(C.4)+(A.3); (I-c)+(C.1)+(A.3); (I-c)+(B.8)+(A.3); (I-c)+(B.1)+(A.4); (I-c)+(C.4)+(A.4); (I-c)+(B.8)+(A.4); (I-c)+(C.4)+(B.1); (I-c)+(C.1)+(B.6); (I-c)+(C.2)+(B.5); (I-c)+(C.2)+(B.6); (I-c)+(C.3)+(B.3); (I-c)+(B.8)+(C.4); (I-c)+(B.2)+(A.4); (I-c)+(C.4)+(A.1); (I-c)+(B.7)+(A.3); (I-c)+(B.7)+(A.4); (I-c)+(C.4)+(A.1); (I-c)+(B.2)+(B.1); (I-c)+(C.4)+(B.2); (I-c)+(B.7)+(B.1); (I-c)+(B.7)+(C.4); (I-c)+(B.6)+(A.4); (I-c)+(B.6)+(A.1); (I-c)+(B.6)+(A.2); (I-c)+(B.5)+(A.1); (I-c)+(B.5)+(A.2); (I-c)+(B.3)+(A.3); (I-c)+(B.3)+(A.4); (I-c)+(B.3)+(A.2); (I-c)+(B.4)+(A.1); (I-c)+(B.4)+(A.2); (I-c)+(C.4)+(B.6); (I-c)+(C.4)+(B.3); (I-c)+(C.1)+(A.4); (I-c)+(C.1)+(A.1); (I-c)+(C.1)+(A.2); (I-c)+(C.1)+(B.1); (I-c)+(C.1)+(B.3); (I-c)+(C.1)+(B.4); (I-c)+(C.3)+(A.3); (I-c)+(C.3)+(A.4); (I-c)+(C.3)+(A.2); (I-c)+(C.3)+(B.1); (I-c)+(C.2)+(A.3); (I-c)+(C.2)+(A.4); (I-c)+(B.8)+(C.1); (I-c)+(B.8)+(C.3); (I-c)+(B.9)+(A.4); (I-c)+(B.9)+(B.1) and (I-c)+(B.9)+(B.6).

Particularly preferred active compound combinations are the following combinations selected from the group consisting of: (I-c)+(B.6)+(A.4); (I-c)+(B.6)+(A.1); (I-c)+(B.6)+(A.2); (I-c)+(B.5)+(A.1); (I-c)+(B.5)+(A.2); (I-c)+(B.3)+(A.3); (I-c)+(B.3)+(A.4); (I-c)+(B.3)+(A.2); (I-c)+(B.4)+(A.1); (I-c)+(B.4)+(A.2); (I-c)+(C.4)+(B.6); (I-c)+(C.4)+(B.3); (I-c)+(C.1)+(A.4); (I-c)+(C.1)+(A.1); (I-c)+(C.1)+(A.2); (I-c)+(C.1)+(B.1); (I-c)+(C.1)+(B.3); (I-c)+(C.1)+(B.4); (I-c)+(C.3)+(A.3); (I-c)+(C.3)+(A.4); (I-c)+(C.3)+(A.2); (I-c)+(C.3)+(B.1); (I-c)+(C.2)+(A.3); (I-c)+(C.2)+(A.4); (I-c)+(B.8)+(C.1); (I-c)+(B.8)+(C.3); (I-c)+(B.9)+(A.4); (I-c)+(B.9)+(B.1) and (I-c)+(B.9)+(B.6).

More preferred active compound combinations are the following combinations selected from the group consisting of: (I-c)+(B.2)+(A.4); (I-c)+(C.4)+(A.1); (I-c)+(B.7)+(A.3); (I-c)+(B.7)+(A.4); (I-c)+(C.4)+(A.1); (I-c)+(B.2)+(B.1); (I-c)+(C.4)+(B.2); (I-c)+(B.7)+(B.1) and (I-c)+(B.7)+(C.4).

Most preferred active compound combinations are the following combinations selected from the group consisting of: (I-c)+(B.1)+(A.3); (I-c)+(B.2)+(A.3); (I-c)+(B.6)+(A.3); (I-c)+(C.4)+(A.3); (I-c)+(C.1)+(A.3); (I-c)+(B.8)+(A.3); (I-c)+(B.1)+(A.4); (I-c)+(C.4)+(A.4); (I-c)+(B.8)+(A.4);

(I-c)+(C.4)+(B.1); (I-c)+(C.1)+(B.6); (I-c)+(C.2)+(B.5); (I-c)+(C.2)+(B.6); (I-c)+(C.3)+(B.3) and (I-c)+(B.8)+(C.4).

In the following further active compound combinations comprising compounds of the general formula (I-d) and compounds selected from the group consisting of (A), (B) and/or (C) are described.

In a first embodiment of the present invention, the compound of the general formula (I-d) is combined with at least one member of (A) the group of inhibitors of the ergosterol biosynthesis and at least one member of (B) the group of inhibitors of the respiratory chain at complex I or II.

In a second embodiment of the present invention, the compound of the general formula (I-d) is combined with at least one member of (A) the group of inhibitors of the ergosterol biosynthesis and at least one member of (C) the group of inhibitors of the respiratory chain at complex III.

In a third embodiment of the present invention, the compound of the general formula (I-d) is combined with at least one member of (B) the group of inhibitors of the respiratory chain at complex I or II and at least one member of (C) the group of inhibitors of the respiratory chain at complex III.

In a fourth embodiment of the present invention, the compound of the general formula (I-d) is combined with at least two distinct members of (A) the group of inhibitors of the ergosterol biosynthesis.

In a fifth embodiment of the present invention, the compound of the general formula (I-d) is combined with at least two distinct members of (B) the group of inhibitors of the respiratory chain at complex I or II.

In a sixth embodiment of the present invention, the compound of the general formula (I-d) is combined with at least two distinct members of (C) the group of inhibitors of the respiratory chain at complex III.

Preferred active compound combinations are the following combinations selected from the group consisting of: (I-d)+(B.1)+(A.3); (I-d)+(B.2)+(A.3); (I-d)+(B.6)+(A.3); (I-d)+(C.4)+(A.3); (I-d)+(C.1)+(A.3); (I-d)+(B.8)+(A.3); (I-d)+(B.1)+(A.4); (I-d)+(C.4)+(A.4); (I-d)+(B.8)+(A.4); (I-d)+(C.4)+(B.1); (I-d)+(C.1)+(B.6); (I-d)+(C.2)+(B.5); (I-d)+(C.2)+(B.6); (I-d)+(C.3)+(B.3); (I-d)+(B.8)+(C.4); (I-d)+(B.2)+(A.4); (I-d)+(C.4)+(A.1); (I-d)+(B.7)+(A.3); (I-d)+(B.7)+(A.4); (I-d)+(C.4)+(A.1); (I-d)+(B.2)+(B.1); (I-d)+(C.4)+(B.2); (I-d)+(B.7)+(B.1); (I-d)+(B.7)+(C.4); (I-d)+(B.6)+(A.4); (I-d)+(B.6)+(A.1); (I-d)+(B.6)+(A.2); (I-d)+(B.5)+(A.1); (I-d)+(B.5)+(A.2); (I-d)+(B.3)+(A.3); (I-d)+(B.3)+(A.4); (I-d)+(B.3)+(A.2); (I-d)+(B.4)+(A.1); (I-d)+(B.4)+(A.2); (I-d)+(C.4)+(B.6); (I-d)+(C.4)+(B.3); (I-d)+(C.1)+(A.4); (I-d)+(C.1)+(A.1); (I-d)+(C.1)+(A.2); (I-d)+(C.1)+(B.1); (I-d)+(C.1)+(B.3); (I-d)+(C.1)+(B.4); (I-d)+(C.3)+(A.3); (I-d)+(C.3)+(A.4); (I-d)+(C.3)+(A.2); (I-d)+(C.3)+(B.1); (I-d)+(C.2)+(A.3); (I-d)+(C.2)+(A.4); (I-d)+(B.8)+(C.1); (I-d)+(B.8)+(C.3); (I-d)+(B.9)+(A.4); (I-d)+(B.9)+(B.1) and (I-d)+(B.9)+(B.6).

Particularly preferred active compound combinations are the following combinations selected from the group consisting of: (I-d)+(B.6)+(A.4); (I-d)+(B.6)+(A.1); (I-d)+(B.6)+(A.2); (I-d)+(B.5)+(A.1); (I-d)+(B.5)+(A.2); (I-d)+(B.3)+(A.3); (I-d)+(B.3)+(A.4); (I-d)+(B.3)+(A.2); (I-d)+(B.4)+(A.1); (I-d)+(B.4)+(A.2); (I-d)+(C.4)+(B.6); (I-d)+(C.4)+(B.3); (I-d)+(C.1)+(A.4); (I-d)+(C.1)+(A.1); (I-d)+(C.1)+(A.2); (I-d)+(C.1)+(B.1); (I-d)+(C.1)+(B.3); (I-d)+(C.1)+(B.4); (I-d)+(C.3)+(A.3); (I-d)+(C.3)+(A.4); (I-d)+(C.3)+(A.2); (I-d)+(C.3)+(B.1); (I-d)+(C.2)+(A.3); (I-d)+(C.2)+(A.4); (I-d)+(B.8)+(C.1); (I-d)+(B.8)+(C.3); (I-d)+(B.9)+(A.4); (I-d)+(B.9)+(B.1) and (I-d)+(B.9)+(B.6).

More preferred active compound combinations are the following combinations selected from the group consisting of: (I-d)+(B.2)+(A.4); (I-d)+(C.4)+(A.1); (I-d)+(B.7)+(A.3); (I-d)+(B.7)+(A.4); (I-d)+(C.4)+(A.1); (I-d)+(B.2)+(B.1); (I-d)+(C.4)+(B.2); (I-d)+(B.7)+(B.1) and (I-d)+(B.7)+(C.4).

Most preferred active compound combinations are the following combinations selected from the group consisting of: (I-d)+(B.1)+(A.3); (I-d)+(B.2)+(A.3); (I-d)+(B.6)+(A.3); (I-d)+(C.4)+(A.3); (I-d)+(C.1)+(A.3); (I-d)+(B.8)+(A.3); (I-d)+(B.1)+(A.4); (I-d)+(C.4)+(A.4); (I-d)+(B.8)+(A.4); (I-d)+(C.4)+(B.1); (I-d)+(C.1)+(B.6); (I-d)+(C.2)+(B.5); (I-d)+(C.2)+(B.6); (I-d)+(C.3)+(B.3) and (I-d)+(B.8)+(C.4).

All named mixing partners of the groups (I), (II) and (III) can, if their functional groups enable this, optionally form salts with suitable bases or acids.

Where a compound (I), (II) or (III) can be present in tautomeric form, such a compound is understood hereinabove and herein below also to include, where applicable, corresponding tautomeric forms, even when these are not specifically mentioned in each case.

The radical definitions and explanations given above in general terms or stated within preferred ranges can, however, also be combined with one another as desired, i.e. including between the preferred, particular preferred, more and most preferred ranges. They apply both to the end products and correspondingly to precursors and intermediates. In addition, individual definitions may not apply.

In the definitions of the symbols given in the above formulae, collective terms were used which are generally representative of the following substituents:

Halogen: (also in combinations such as haloalkyl, haloalkoxy etc.) fluorine, chlorine, bromine and iodine;

Alkyl: (including in combinations such as alkylthio, alkoxy etc.) saturated, straight-chain or branched hydrocarbyl radicals having 1 to 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.

Haloalkyl: (including in combinations such as haloalkylthio, haloalkoxy etc.) straight-chain or branched alkyl groups having 1 to 8 carbon atoms (as specified above), where some or all of the hydrogen atoms in these groups may be replaced by halogen atoms as specified above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl: unsaturated, straight-chain or branched hydrocarbyl radicals having 2 to 8 carbon atoms and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Cycloalkyl: monocyclic saturated hydrocarbyl groups having 3 to 8 carbon ring members, such as cyclopropyl, cyclobutyl, cyclopentyl, cyclohexyl, cycloheptyl and cyclooctyl.

Aryl: unsubstituted or substituted, aromatic, mono-, bi- or tricyclic ring, for example phenyl, naphthyl, anthracenyl (anthryl), phenanthracenyl (phenanthryl).

Hetaryl: unsubstituted or substituted, unsaturated heterocyclic 5- to 7-membered ring containing up to 4 nitrogen atoms or alternatively 1 nitrogen atom and up to 2 further heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

Composition/Formulation

The present invention further relates to a crop protection composition for controlling harmful microorganisms, especially phytopathogenic fungi, comprising an effective and non-phytotoxic amount of the inventive active compound combinations. These are preferably fungicidal crop protection compositions which comprise agriculturally suitable auxiliaries, solvents, carriers, surfactants, extenders or the like.

An "effective and non-phytotoxic amount" means an amount of the inventive active compound combination or composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive active compound combinations or compositions.

The treatment is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching) and drip irrigating. It is also possible to deploy the compositions by the ultra-low volume method or to inject the composition preparation or the compositions itself into the soil.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active compound combinations are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essential: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy- and propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and copolymerisates of (meth)acrylic acid and (meth)acrylic acid esters, and further co-polymerisates of methacrylic acid and methacrylic acid esters which are neutralized with alkalimetal hydroxide and also condensation products of optionally substituted naphthalene sulfonic acid salts with formaldehyde.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures thereof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active compound combinations or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active compound combinations may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active compound combinations or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active compound combinations by the ultra-low volume method or to inject the active compound combination preparation into the soil.

Plant/Crop Protection

The inventive active compound combinations or compositions have potent microbicidal activity and can be used for control of harmful microorganisms, such as phytopathogenic fungi, in crop protection and in the protection of materials.

The invention also relates to a method for controlling harmful microorganisms, comprising applying the active compound combination or the crop protection composition to the plant or the phytopathogenic fungi or the habitat of the plant or the habitat of the phytopathogenic fungi.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*;

*Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; *Eutypa* dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plamodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

In particular, the active compound combinations and compositions according to the invention are suitable for controlling the following plant diseases: *Albugo* spp. (white rust) on ornamental plants, vegetable crops (e.g. *A. candida*) and sunflowers (e.g. *A. tragopogonis*); *Alternaria* spp. (black spot disease, black blotch) on vegetables, oilseed rape (e.g. *A. brassicola* or *A. brassicae*), sugar beet (e.g. *A. tenuis*), fruit, rice, soybeans and also on potatoes (e.g. *A. solani* or *A. alternata*) and tomatoes (e.g. *A. solani* and *A. alternata*) and *Alternaria* spp. (black head) on wheat; *Aphanomyces* spp. on sugar beet and vegetables; *Ascochyta* spp. on cereals and vegetables, e.g. *A. tritici* (*Ascochyta* leaf blight) on wheat and *A. hordei* on barley; *Bipolaris* and *Drechslera* spp. (teleomorph: *Cochliobolus* spp.), e.g. leaf spot diseases (*D. maydis* and *B. zeicola*) on corn, e.g. glume blotch (*B. sorokiniana*) on cereals and e.g. *B. oryzae* on rice and on lawn; *Blumeria* (old name: *Erysiphe*) *graminis* (powdery mildew) on cereals (e.g. wheat or barley); *Botryosphaeria* spp. ('Slack Dead Arm Disease') on grapevines (e.g. *B. obtusa*); *Botrytis cinerea* (teleomorph: *Botryotinia fuckeliana*: gray mold, gray rot) on soft fruit and pomaceous fruit (inter alia strawberries), vegetables (inter alia lettuce, carrots, celeriac and cabbage), oilseed rape, flowers, grapevines, forest crops and wheat (ear mold); *Bremia lactucae* (downy mildew) on lettuce; *Ceratocystis* (syn. *Ophiostoma*) spp. (blue stain fungus) on deciduous trees and coniferous trees, e.g. *C. ulmi* (Dutch elm disease) on elms; *Cercospora* spp. (*Cereospora* leaf spot) on corn (e.g. *C. zeae-maydis*), rice, sugar beet (e.g. *C. beticola*), sugar cane, vegetables, coffee, soybeans (e.g. *C. sojina* or *C. kikuchil*) and rice; *Cladosporium* spp. on tomato (e.g. *C. fulvum*: tomato leaf mold) and cereals, e.g. *C. herbarum* (ear rot) on wheat; *Claviceps purpurea* (ergot) on cereals; *Cochliobolus* (anamorph: *Helminthosporium* or *Bipolaris*) spp. (leaf spot) on corn (e.g. *C. carbonum*), cereals (e.g. *C. sativus*, anamorph: *B. sorokiniana*: glume blotch) and rice (for example *C. miyabeanus*, anamorph: *H. oryzae*); *Colletotrichum* (teleomorph: *Glomerella*) spp. (anthracnosis) on cotton (e.g. *C. gossypii*), corn (e.g. *C. graminicola*: stem rot and anthracnosis), soft fruit, potatoes (e.g. *C. coccodes*: wilt disease), beans (e.g. *C. lindemuthianum*) and soybeans (e.g. *C. truncatum*); *Corticium* spp., e.g. *C. sasakii* (sheath blight) on rice; *Corynespora cassiicola* (leaf spot) on soybeans and ornamental plants; *Cycloconium* spp., e.g. *C. oleaginum* on olives; *Cylindrocarpon* spp. (e.g. fruit tree cancer or black foot disease of grapevine, teleomorph: *Nectria* or *Neonectria* spp.) on fruit trees, grapevines (e.g. *C. liriodendn*; teleomorph: *Neonectria liriodendri*, black foot disease) and many ornamental trees; *Dematophora* (teleomorph: *Rosellinia*) *necatrix* (root/stem rot) on soybeans; *Diaporthe* spp. e.g. *D. phaseolorum* (stem disease) on soybeans; *Drechslera* (syn. *Helminthosporium*, teleomorph: *Pyrenophora*) spp. on corn, cereals, such as barley (e.g. *D. teres*, net blotch) and on wheat (e.g. *D. tritici-repentis*: DTR leaf spot), rice and lawn; Esca disease (dieback of grapevine, apoplexia) on grapevines, caused by *Formitiporia* (syn. *Phellinus*) *punctata, F mediterranea. Phaeomoniella chlamydospora* (old name *Phaeoacremonium chlamydosporum*), *Phaeoacremonium aleophilum* and/or *Botryosphaeria obtusa; Elsinoe* spp. on pome fruit (*E. pyri*) and soft fruit (*E. veneta*: anthracnosis) and also grapevines (*E. ampelina*: anthracnosis); *Entyloma oryzae* (leaf smut) on rice; *Epicoccum* spp. (black head) on wheat; *Erysiphe* spp. (powdery mildew) on sugar beet (*E. betae*), vegetables (e.g. *E. pisi*), such as cucumber species (e.g. *E. cichoracearum*) and cabbage species, such as oilseed rape (e.g. *E. cruciferarum*); *Eutypa fata* (*Eutypa* cancer or dieback, anamorph: *Cytosporina lata*, syn. *Libertella blepharis*) on fruit trees, grapevines and many ornamental trees; *Exserohilum* (syn. *Helminthosporium*) spp. on corn (e.g. *E. turcicum*); *Fusarium* (teleomorph: *Gibberella*) spp. (wilt disease, root and stem rot) on various plants, such as e.g. *F. graminearum* or *F. culmorum* (root rot and silver-top) on cereals (e.g. wheat or barley), *F. oxysporum* on tomatoes, *F. solani* on soybeans and *F. verticillioides* on corn; *Gaeumannomyces graminis* (takeall) on cereals (e.g. wheat or barley) and corn; *Gibberella* spp. on cereals (e.g. *G. zeae*) and rice (e.g. *G. fujikuroi*: bakanae disease); *Glomerella cingulata* on grapevines, pomaceous fruit and other plants and *G. gossypii* on cotton; grainstaining complex on rice; *Guignardia bidwellii* (black rot) on grapevines; *Gymnosporangium* spp. on *Rosaceae* and juniper, e.g. *G. sabinae* (pear rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on grapevines; *Macrophomina phaseolina* (syn. *phaseoli*) (root/stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa. M. fructicola* and *M. fructigena* (blossom and twig blight) on stone fruit and other *Rosaceae*; *Mycosphaerella* spp. on cereals, bananas, soft fruit and peanuts, such as e.g. *M. graminicola* (anamorph: *Septoria tritici, Septoria* leaf blotch) on wheat or *M. fijiensis* (Sigatoka disease) on bananas; *Peronospora* spp. (downy mildew) on cabbage (e.g. *P. brassicae*), oilseed rape (e.g. *P. parasitica*), bulbous plants (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on grapevines (e.g. *P. tracheiphila* and *P. tetraspora*) and soybeans (e.g. *P. gregata*: stem disease); *Phoma lingam* (root and stem rot) on oilseed rape and cabbage and *P. betae* (leaf spot) on sugar beet; *Phomopsis* spp. on sunflowers, grapevines (e.g. *P. viticola*: dead-arm disease) and soybeans (e.g. stem canker/stem blight: *P. phaseoli*, teleomorph: *Diaporthe phaseolorum*); *Physoderma maydis* (brown spot) on corn; *Phytophthora* spp. (wilt disease, root, leaf, stem and fruit rot) on various plants, such as on bell peppers and cucumber species (e.g. *P. capsici*), soybeans (e.g. *P. megasperma*, syn. *P. sojae*), potatoes and tomatoes (e.g. *P. infestans*. late blight and brown rot) and deciduous trees (e.g. *P. ramorum* sudden oak death); *Plasmodiophora brassicae* (club-root) on cabbage, oilseed rape, radish and other plants; *Plasmopara* spp., e.g. *P. viticola* (*peronospora* of grapevines, downy mildew) on grapevines and *P. halstedii* on sunflowers; *Podosphaera* spp. (powdery mildew) on *Rosaceae*, hops, pomaceaus fruit and soft fruit, e.g. *P. leucotricha* on apple; *Polymyxa* spp., e.g. on cereals, such as barley and wheat (*P. graminis*) and sugar beet (*P. betae*) and the viral diseases transmitted thereby; *Pseudocercosporella herpotrichoides* (eyespot/stem break, teleomorph: *Tapesia yallundae*) on cereals. e.g. wheat or barley; *Pseudoperonospora* (downy mildew) on various plants, e.g. *P. cubensis* on cucumber species or *P. humili* on hops; *Pseudopezicula tracheiphila* (angular leaf scorch, anamorph *Phialophora*) on grapevines; *Puccinia* spp. (rust disease) on various plants, e.g. *P. triticina* (brown rust of wheat), *P. striiformis* (yellow rust). *P. hordei* (dwarf leaf rust), *P. graminis* (black rust) or *P. recondita* (brown rust of rye) on cereals, such as e.g. wheat, barley or rye. *P. kuehnii* on sugar cane and, e.g., on asparagus (e.g. *P. asparagi*); *Pyrenophora* (anamorph: *Drechslera*) *tritici-repentis* (speckled leaf blotch) on wheat or *P. teres* (net blotch) on barley; *Pyricularia* spp., e.g. *P. oryzae* (teleomorph: *Magnaporthe grisea*. rice blast) on rice and *P. grisea* on lawn and cereals; *Pythium* spp. (damping-off disease) on lawn, rice, corn, wheat, cotton, oilseed rape, sunflowers, sugar beet, vegetables and other plants (e.g. *P. ultimum* or *P. aphanidermatum*); *Ramularia* spp., e.g. *R. collo-cygni* (*Ramularia* leaf and lawn spot/physiological leaf spot) on barley and *R. bet/cola* on sugar beet; *Rhizoctonia* spp. on cotton, rice, potatoes, lawn, corn, oilseed rape, potatoes, sugar beet, vegetables and on various other plants, for example *R. solani* (root and stern rot) on soybeans, *R. solani* (sheath blight) on rice or *R. cerealis* (sharp eyespot) on wheat or barley;

*Rhizopus stolonifer* (soft rot) on strawberries, carrots, cabbage, grapevines and tomato; *Rhynchosporium secalis* (leaf spot) on barley, rye and triticale; *Sarocladium oryzae* and *S. attenuatum* (sheath rot) on rice; *Sclerotinia* spp. (stem or white rot) on vegetable and field crops, such as oilseed rape, sunflowers (e.g. *Sclerotinia sclerotiorum*) and soybeans (e.g. *S. rolfsii*), *Septoria* spp. on various plants, e.g. *S. glycines* (leaf spot) on soybeans, *S. tritici* (*Septoria* leaf blotch) on wheat and *S.* (syn. *Stagonospora*) *nodorum* (leaf blotch and glume blotch) on cereals; *Uncinula* (syn. *Erysiphe*) *necator* (powdery mildew, anamorph: *Oidium tuckeri*) on grapevines; *Setospaeria* spp. (leaf spot) on corn (e.g. *S. turcicum*, syn. *Helminthosporium turcicum*) and lawn; *Sphacelotheca* spp. (head smut) on corn, (e.g. *S. reiliana*: kernel smut), millet and sugar cane; *Sphaerotheca fuliginea* (powdery mildew) on cucumber species; *Spongospora subterranea* (powdery scab) on potatoes and the viral diseases transmitted thereby; *Stagonospora* spp. on cereals, e.g. *S. nodorum* (leaf blotch and glume blotch, teleomorph: *Leptosphaeria* [syn. *Phaeosphaeria] nodorum*) on wheat; *Synchytrium endobioticum* on potatoes (potato wart disease); *Taphrina* spp., e.g. *T. deformans* (curly-leaf disease) on peach and *T. pruni* (plum-pocket disease) on pi ums; *Thielaviopsis* spp. (black root rot) on tobacco, pome fruit, vegetable crops, soybeans and cotton, e.g. *T. basicola* (syn. *Chalara elegans*); *Tilletia* spp. (bunt or stinking smut) on cereals, such as e.g. *T. tritici* (syn. *T. caries*, wheat bunt) and *T. controversa* (dwarf bunt) on wheat; *Typhula incarnata* (gray snow mold) on barley or wheat; *Urocystis* spp., e.g. *U. occulta* (flag smut) on rye; *Uromyces* spp. (rust) on vegetable plants, such as beans (e.g. *U. appendiculatus*, syn. *U. phaseoli*) and sugar beet (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears and *Verticillium* spp. (leaf and shoot wilt) on various plants, such as fruit trees and ornamental trees, grapevines, soft fruit, vegetable and field crops, such as e.g. *V. dahliae* on strawberries, oilseed rape, potatoes and tomatoes.

The present invention is also directed to the use of the active compound combinations or compositions according to the invention for the treatment of soybean diseases. The following diseases of soybeans can be controlled with preference: Fungal diseases on leaves, stems, pods and seeds caused, for example, by *Alternaria* leaf spot (*Alternaria spec. atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*). Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neo-*

*cosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The present invention is also directed to the use of the active compound combinations or compositions according to the invention for the treatment of cereal diseases. The following diseases of cereals can be controlled with preference: *Ascochyta* leaf blight (*Ascochyta tritici* on wheat and *A. hordei* on barley), Powdery mildew (e.g. *Blumeria graminis* f. sp. *tritici* on wheat and *B. graminis* f. sp. *hordei* on barley; Ergot (*Claviceps purpurea*) (ergot); Net blotch (e.g. *Pyrenophora teres* on barley); DTR leaf spot (e.g. *D. triticirepentis* on wheat); *Fusarium* head blight (e.g. *F. graminearum* or *F. culmorum*); takeall (*Gaeumannomyces graminis*); Snow mould (*Microdochium* (syn. *Fusarium*) *nivale*); *Septoria* leaf blotch (*Mycosphaerella graminicola*—anamorph: *Septoria tritici*); Eyespot (*Pseudocercosporella herpotrichoides*, teleomorph: *Tapesia yallundae*), brown rust (e.g. *P. triticina* on wheat), yellow rust (*P. striiformis*); dwarf leaf rust (*P. hordei*), black rust (*Puccinia graminis*); *Ramularia* leaf spot (*Ramularia collo-cygni*); sharpe eye spot (*R. cerealis*) *Rhynchosporium* leaf spot (*Rhynchosporium secalis*); *Septoria* glume blotch (*Septoria nodorum*); Smut & bunt diseases (e.g. *T. tritici* and *T. controversa*); gray snow mold (*Typhula incarnata*); loose smuts (e.g. *U. nuda* and *U. avenae*).

Most preference is given to the following soybean diseases: *Cercospora kikuchii, Cercospora sojina; Colletotrichum gloeosporoides dematium* var. *truncatum; Corynespora casiicola; Diaporthe phaseolorum; Microsphaera diffusa; Peronospora manshurica; Phakopsora* species, for example *Phakopsora pachyrhizi* and *Phakopsora meibomiae* (soybean rust); *Phytophthora megasperma; Phialophora gregata; Rhizoctonia solani; Sclerotinia sclerotiorum; Septoria* spp. e.g. *Septoria glycines, Thielaviopsis basicola*.

Most preference is given to the following cereal diseases: *Blumeria graminis* f. sp. *hordei Blumeria graminis* f. sp. *tritici F. graminearum F. culmorum Gaeumannomyces graminis Microdochium nivale M. graminicola* (anamorph: *Septoria tritici*) *Pseudocercosporella herpotrichoides P. triticina P. striiformis P. hordei P. graminis P. recondita Pyrenophora tritici-repentis Pyrenophora teres Ramularia collo-cygni Rhizoctonia cerealis Rhynchosporium secalis Septoria nodorum*.

The fact that the active compound combinations or compositions are well tolerated by plants at the concentrations required for controlling plant diseases allows the treatment of above-ground parts of plants, of propagation stock and seeds, and of the soil.

According to the invention all plants and plant parts can be treated. By "plants" is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By "plant parts" is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active compound combinations or compositions, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Plant Growth Regulation

In some cases, the active compound combinations or compositions can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The inventive active compound combinations intervene in the metabolism of the plants and can therefore also be used as growth regulators.

Plant growth regulators may exert various effects on plants. The effect of the substances depends essentially on the time of application in relation to the developmental stage of the plant, and also on the amounts of active compound combination or composition applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composite of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active compound combinations or compositions according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compound combinations or compositions according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance.

Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:

Improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

Further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

Further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

And further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composite and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci*. Vol. 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology*, 2007, 11, 319-341; *Applied Soil Ecology*, 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal active compound combinations or compositions of the present invention relates to a combined use of a) reducing damage of plants and plant parts or losses in harvested fruits or vegetables caused by phytopathogenic fungi by controlling such phytopathogenic fungi, with or without resistance management, and b) at least one of enhanced root growth, improved greening, improved water use efficiency, delayed senescence and enhanced yield.

Seed Treatment

The invention further comprises a method for treating seed.

The invention further relates to seed which has been treated by one of the methods described in the previous paragraph. The inventive seeds are employed in methods for the protection of seed from harmful microorganisms such as e.g. phytopathogenic fungi. In these methods, seed treated with at least one inventive active compound combination is used.

The inventive active compound combinations or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active compound combination used so as to provide the best possible protection for the seed and the germinating plant from attack by phytopathogenic fungi, but without damaging the plant itself by the active compound combination employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active compound combinations and compositions mean that treatment of the seed with these active compound combinations and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active compound combinations or compositions can especially also be used with transgenic seed, in which case the plant growing from this seed is capable of expressing a protein which acts against plant pests and/or phytopathogenic fungi. By virtue of the treatment of such seed with the inventive active compound combinations or compositions, merely the expression of the protein, for example an insecticidal protein, can control certain plant pests and/or phytopathogenic fungi. Surprisingly, a further synergistic effect can be observed in this case, which additionally increases the effectiveness for protection against attack by plant pests and/or phytopathogenic fungi.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active compound combinations or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European maize borer and/or the Western maize rootworm. The heterologous gene more preferably originates from *Bacillus thuringiensis*.

In the context of the present invention, the active compound combination is applied to the seed alone or in a suitable formulation (i.e. as a composition). Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the active compound combination or composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive active compound combinations can be applied directly, i.e. without containing any other components and without having been diluted. In general, it is preferable to apply the active compound combinations to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active compound combinations usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active compound combinations with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in crop protection compositions. Examples include dichlorophene and benzyl alcohol hemiformal.

Secondary thickeners which may be present in the seed dressing formulations usable in accordance with the invention are all substances usable for such purposes in crop protection compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive active compound combinations or compositions can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive active compound combinations or compositions can also be used in the protection of materials, for protection of industrial materials against attack and destruction by harmful microorganisms, for example fungi and insects.

In addition, the active compound combinations or compositions can be used as antifouling compositions, alone or in combinations with other active ingredients.

Industrial materials in the present context are understood to mean inanimate materials which have been prepared for use in industry. For example, industrial materials which are to be protected by inventive active compound combinations from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active compound combinations or compositions may prevent adverse effects, such as rotting, decay, discoloration, decoloration or formation of mould.

In the case of treatment of wood the active compound combinations or compositions according to the invention may also be used against fungal diseases liable to grow on or inside timber. The term "timber" means all types of species of wood, and all types of working of this wood intended for construction, for example solid wood, highdensity wood, laminated wood, and plywood. The method for treating timber according to the invention mainly consists in contacting one or more active compound combinations or compositions according to the invention; this includes for example direct application, spraying, dipping, injection or any other suitable means.

In addition, the active compound combinations or compositions can be used to protect objects which come into contact with saltwater or brackish water, especially hulls, screens, nets, buildings, moorings and signalling systems, from fouling.

The inventive method for controlling phytopathogenic fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active compound combinations or compositions may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active compound combinations preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma virile; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active compound combinations also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive active compound combinations can therefore be used both in medical and in non-medical applications Genetically Modified Organisms As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi-technology or microRNA—miRNA-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compound combinations and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

The active compound combinations or compositions according to the invention also have a strengthening effect in plants. Accordingly, they are also suitable for mobilizing the defense system of the plant against attack by harmful microorganisms. This may, if appropriate, be one of the reasons of the enhanced activity of the active compound combinations or compositions according to the invention. Plant-strengthening (resistance-inducing) substances are to be understood as meaning, in the present context, those substances or combinations of substances which are capable of stimulating the defense system of plants in such a way that, when subsequently inoculated with harmful microorganisms, the treated plants display a substantial degree of resistance to these microorganisms. In the present case, harmful microorganisms are to be understood as meaning phytopathogenic fungi. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compound combination or composition.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode or insect resistant plants are for example those mentioned in WO 2012/045798 A1 and WO 2012/089757 A1.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 2005/002324, WO 2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means, for example those mentioned in WO 2012/045798 A1 and WO 2012/089757 A1.

Other herbicide resistant plants are for example plants that are made tolerant to herbicides inhibiting the enzyme glutamine synthase, such as bialaphos, phosphinothricin or glufosinate. Such plants can be obtained for example by methods mentioned in WO 2012/045798 A1 and WO 2012/089757 A1.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme, for example as mentioned in WO 2012/045798 A1 and WO 2012/089757 A1.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides (see the corresponding references mentioned in WO 2012/045798 A1 and WO 2012/089757 A1.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, in particular relates to the insect-resistant transgenic plants mentioned in WO 2012/045798 A1 and WO 2012/089757 A1.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants are those mentioned in WO 2012/045798 A1 and WO 2012/089757 A1.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such those from transgenic plants mentioned in WO 2012/045798 A1 and WO 2012/089757 A1.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include the oilseed rape plants mentioned in WO 2012/045798 A1 and WO 2012/089757 A1.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending.

Particularly useful transgenic plants which may be treated according to the invention are plants containing transformation events, or a combination of transformation events, are those mentioned in WO 2012/045798 A1 and WO 2012/089757 A1.

Application Rates and Timing

The compounds of the formula (I) and the compounds (II) and (III) of the active compound combination or composition according to the present invention can be combined in any specific ratio between these three mandatory components.

In the active compound combinations or compositions according to the invention the compounds (I) and (II) or the compounds (I) and (III) or the compounds (II) and (III) are present in a synergistically effective weight ratio of I:II or I:III or II:III in a range of 100:1 to 1:100, preferably in a weight ratio of 50:1 to 1:50, most preferably in a weight ratio of 30:1 to 1:30.

In preferred embodiments of the invention the weight ratio of I:II is from 1:1 to 1:20, preferably from 1:1 to 1:10, more preferably from 1:1 to 1:5, most preferably from 1:1 to 1:2.

In preferred embodiments of the invention the weight ratio of I:III is from 1:1 to 1:10, preferably from 1:1 to 1:5, more preferably from 1:1 to 1:2.

In preferred embodiments of the invention the weight ratio of II:III is from 20:1 to 1:20, preferably from 10:1 to 1:10, more preferably from 5:1 to 1:5, most preferably from 2:1 to 1:2.

In preferred embodiments of the invention the weight ratio of I:II is from 1:1 to 1:20 and the weight ratio of I:III is from 1:1 to 1:10, preferably the weight ratio of I:II is from 1:1 to 1:10 and the weight ratio of I:III is from 1:1 to 1:5, more preferably the weight ratio of I:II is from 1:1 to 1:5 and the weight ratio of I:III is from 1:1 to 1:2, most preferably the weight ratio of I:II is from 1:1 to 1:2 and the weight ratio of I:III is from 1:1 to 1:2.

In preferred embodiments of the invention the weight ratio of I:II is from 1:1 to 1:20 and the weight ratio of II:III is from 20:1 to 1:20, preferably the weight ratio of I:II is from 1:1 to 1:10 and the weight ratio of II:III is from 10:1 to 1:10, more preferably the weight ratio of I:II is from 1:1 to 1:5 and the weight ratio of II:III is from 5:1 to 1:5, most preferably the weight ratio of I:II is from 1:1 to 1:2 and the weight ratio of II:III is from 2:1 to 1:2.

In preferred embodiments of the invention the weight ratio of I:III is from 1:1 to 1:10 and the weight ratio of II:III is from 20:1 to 1:20, preferably the weight ratio of I:III is from 1:1 to 1:5 and the weight ratio of II:III is from 10:1 to 1:10, more preferably the weight ratio of I:III is from 1:1 to 1:2 and the weight ratio of II:III is from 5:1 to 1:5, most preferably the weight ratio of I:III is from 1:1 to 1:2 and the weight ratio of II:III is from 2:1 to 1:2.

In preferred embodiments of the invention the weight ratio of I:II is from 1:1 to 1:20, the weight ratio of I:III is from 1:1 to 1:10 and the weight ratio of II:III is from 20:1 to 1:20, preferably the weight ratio of I:II is from 1:1 to 1:10, the weight ratio of I:III is from 1:1 to 1:5 and the weight ratio of II:III is from 10:1 to 1:10, more preferably the weight ratio of I:II is from 1:1 to 1:5, the weight ratio of I:III is from 1:1 to 1:2 and the weight ratio of II:III is from 5:1 to 1:5, most preferably the weight ratio of I:II is from 1:1 to 1:2, the weight ratio of I:III is from 1:1 to 1:2 and the weight ratio of II:III is from 2:1 to 1:2.

When using the inventive active compound combinations or compositions as fungicides, the application rates can be varied within a relatively wide range, depending on the kind of application. The application rate of the inventive active compound combinations or compositions is in the case of treatment of plants or plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, in the case of soil treatment: from 0.1 to 10 000 g/ha, preferably from 1 to 5000 g/ha.

These application rates are merely by way of example and are not limiting for the purposes of the invention.

The inventive active compound combinations or compositions can thus be used to protect plants from attack by the pathogens mentioned above for a certain period of time after treatment. The period for which protection is provided extends generally for 1 to 28 days, preferably for 1 to 14 days, more preferably for 1 to 10 days, most preferably for 1 to 7 days, after the treatment of the plants with the active compound combinations, or for up to 200 days after a seed treatment.

The method of treatment according to the invention also provides the use or application of compounds (I) and (II) and (III) in a simultaneous, separate or sequential manner. If the single active ingredients are applied in a sequential manner, i.e. at different times, they are applied one after the other within a reasonably short period, such as a few hours or days. Preferably the order of applying the compounds (I) and (II) and (III) is not essential for working the present invention.

The plants listed above can particularly advantageously be treated in accordance with the invention with the active compound combinations or compositions. The preferred ranges stated above for the active compound combinations or compositions also apply to the treatment of these plants. Particular emphasis is given to the treatment of plants with the active compound combinations or compositions specifically mentioned in the present description. As mentioned above the mixing ratio is preferably to be chosen such that a synergistic active compound combination is obtained. A synergistic effect of fungicides is always present when the fungicidal activity of the active compound combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", *Weeds* 1967, 15, 20-22):

If
X is the efficacy when active compound (I) is applied at an application rate of m ppm (or g/ha),
Y is the efficacy when active compound (II) is applied at an application rate of n ppm (or g/ha),
Z is the efficacy when active compound (III) is applied at an application rate of r ppm (or g/ha),
$E_1$ is the efficacy when the active compounds (I) and (II) are applied at application rates of m and n ppm (or g/ha), respectively, and
$E_2$ is the efficacy when the active compounds (I), (II) and (III) are applied at application rates of m, n and r ppm (or g/ha), respectively, and then $$E_1 = X + Y - \frac{X \cdot Y}{100}$$

and for a ternary active compound combination:

$$E_2 = X + Y + Z - \left(\frac{X \cdot Y + X \cdot Z + Y \cdot Z}{100}\right) + \frac{X \cdot Y \cdot Z}{10000}$$

The degree of efficacy, expressed in % is denoted. 0% means an efficacy which corresponds to that of the control while an efficacy of 100% means that no disease is observed.

If the actual fungicidal activity exceeds the calculated value, then the activity of the active compound combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the following examples. However the invention is not limited to the examples.

Example A: In Vivo Preventive Test on *Alternaria* Test (Tomatoes)

| Solvent: | 24.5 | parts by weight of acetone |
|---|---|---|
|  | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Alternaria solani*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed. The table below clearly shows that the observed activity of the active compound combination according to the invention is greater than the calculated activity, i.e. a synergistic effect is present.

TABLE A1 in vivo preventive test on *Alternaria* test (tomatoes)

| | Active compounds | | Application rate of active compound in ppm a.i. | Efficacy in % found* | calc. | diff.* |
|---|---|---|---|---|---|---|
| (I-d) | N'-(2,5-dimethyl-4-phenoxyphenyl)-N-ethyl-N-methylimidoformamide | | 1 | 15 | | |
| | | | 0.5 | 8 | | |
| (A.4) | tebuconazole | | 1 | 0 | | |
| (B.1) | bixafen | | 1 | 40 | | |
| (C.4) | trifloxystrobin | | 1 | 30 | | |
| (B.8) | N-(5-chloro-2-isopropylbenzyl)-N-cyclopropyl-3-(difluoromethyl)-5-fluoro-1-methyl-1H-pyrazole-4-carboxamide | | 1 | 45 | | |
| (I-d) + (A.4) + (B.1) | 1:1:1 | | 1 + 1 + 1 | 73 | 49 | 24 |
| (I-d) + (A.4) + (C.4) | 1:1:1 | | 1 + 1 + 1 | 60 | 41 | 19 |
| (I-d) + (A.4) + (B.8) | 1:2:2 | | 0.5 + 1 + 1 | 65 | 49 | 16 |

*found = activity found
**calc. = activity calculated using Colby's formula
***diff. = difference between activity found and activity calculated

TABLE A2 in vivo preventive test on *Alternaria* test (tomatoes)

| | Active compounds | | Application rate of active compound in ppm a.i. | Efficacy in % found* | calc. | diff* |
|---|---|---|---|---|---|---|
| (I-d) | N'-(2,5-dimethyl-4-phenoxyphenyl)-N-ethyl-N-methylimidoformamide | | 0.2 | 0 | | |
| | | | 0.1 | 0 | | |
| (A.3) | prothioconazole | | 4 | 24 | | |
| | | | 2 | 0 | | |
| (B.2) | fluopyram | | 2 | 30 | | |
| (B.6) | benzovindiflupyr | | 0.5 | 22 | | |
| (C.1) | azoxystrobin | | 1 | 46 | | |
| (C.4) | trifloxystrobin | | 4 | 73 | | |
| (I-d) + (A.3) + (B.2) | 1:20:20 | | 0.1 + 2 + 2 | 88 | 30 | 58 |
| (I-d) + (A.3) + (B.6) | 1:20:5 | | 0.1 + 2 + 0.5 | 78 | 22 | 56 |
| (I-d) + (A.3) + (C.1) | 1:20:10 | | 0.1 + 2 + 1 | 95 | 46 | 49 |
| (I-d) + (A.3) + (C.4) | 1:20:20 | | 0.2 + 4 + 4 | 88 | 79 | 9 |

*found = activity found
**calc. = activity calculated using Colby's formula
***diff. = difference between activity found and activity calculated Example B: In Vivo Preventive *Blumeria* Test (Barley)

| Solvent: | 49 | parts by weight of N,N-dimethylacetamide |
|---|---|---|
| Emulsifier: | 1 | part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are dusted with spores of *Blumeria graminis* f.sp. *hordei*. The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE B1 in vivo preventive Blumeria test (barley)

|  | Active compounds | Application rate of active compound in ppm a.i. | Efficacy in % | | |
|---|---|---|---|---|---|
|  |  |  | found* | calc.** | diff.*** |
| (I-d) | N'-(2,5-dimethyl-4-phenoxyphenyl)-N-ethyl-N-methylimidoformamide | 40 | 33 | | |
| (B.6) | benzovindiflupyr | 40 | 11 | | |
| (C.2) | picoxystrobin | 20 | 44 | | |
| (I-d) + (A.3) + (C.2) 2:2:1 |  | 40 + 40 + 20 | 78 | 67 | 11 |

*found = activity found
**calc. = activity calculated using Colby's formula
***diff. = difference between activity found and activity calculated

TABLE B2 in vivo preventive Blumeria test (barley)

|  | Active compounds | Application rate of active compound in ppm a.i. | Efficacy in % | | |
|---|---|---|---|---|---|
|  |  |  | found* | calc.** | diff.*** |
| (I-d) | N'-(2,5-dimethyl-4-phenoxyphenyl)-N-ethyl-N-methylimidoformamide | 80 | 22 | | |
|  |  | 40 | 0 | | |
|  |  | 20 | 0 | | |
|  |  | 10 | 0 | | |
| (A.3) | prothioconazole | 40 | 22 | | |
|  |  | 10 | 22 | | |
| (B.1) | bixafen | 40 | 0 | | |
| (B.2) | fluopyram | 40 | 11 | | |
| (C.4) | trifloxystrobin | 10 | 11 | | |
| (I-d) + (A.3) + (B.1) 2:1:1 |  | 80 + 40 + 40 | 100 | 39 | 61 |
| (I-d) + (A.3) + (B.1) 1:1:1 |  | 40 + 40 + 40 | 78 | 22 | 56 |
| (I-d) + (A.3) + (B.2) 2:1:1 |  | 80 + 40 + 40 | 89 | 46 | 43 |
| (I-d) + (A.3) + (B.2) 1:1:1 |  | 40 + 40 + 40 | 89 | 31 | 58 |
| (I-d) + (A.3) + (C.4) 2:1:1 |  | 20 + 10 + 10 | 44 | 31 | 13 |
| (I-d) + (A.3) + (C.4) 1:1:1 |  | 10 + 10 + 10 | 67 | 31 | 36 |

*found = activity found
**calc. = activity calculated using Colby's formula
***diff. = difference between activity found and activity calculated Example C: In Vivo Preventive *Leptosphaeria nodorum* Test (Wheat)

| Solvent: | 49 | parts by weight of N,N-dimethylacetamide |
|---|---|---|
| Emulsifier: | 1 | part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are sprayed with a spore suspension of *Leptosphaeria nodorum*. The plants remain for 48 hours in an incubation cabinet at approximately 20° C. and a relative atmospheric humidity of approximately 100%. The plants are placed in the greenhouse at a temperature of approximately 25° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE C1 in vivo preventive *Leptosphaeria nodorum* test (wheat)

|  | Active compounds | Application rate of active compound in ppm a.i. | Efficacy in % | | |
|---|---|---|---|---|---|
|  |  |  | found* | calc.** | diff.*** |
| (I-d) | N'-(2,5-dimethyl-4-phenoxyphenyl)-N-ethyl-N-methylimidoformamide | 80 | 29 | | |
| (B.1) | bixafen | 80 | 0 | | |

TABLE C1-continued in vivo preventive *Leptosphaeria nodorum* test (wheat)

|  | Active compounds | Application rate of active compound in ppm a.i. | Efficacy in % | | |
|---|---|---|---|---|---|
|  |  |  | found* | calc.** | diff.*** |
| (B.3) | fluxapyroxad | 40 | 14 | | |
| (B.8) | N-(5-chloro-2-isopropylbenzyl)-N-cyclopropyl-3-(difluoromethyl)-5-fluoro-1-methyl-1H-pyrazole-4-carboxamide | 20 | 0 | | |
| (C.3) | pyraclostrobin | 40 | 57 | | |
| (C.4) | trifloxystrobin | 40 | 14 | | |
| (I-d) + (B.1) + (C.4) 2:2:1 | | 80 + 80 + 40 | 71 | 39 | 32 |
| (I-d) + (B.3) + (C.3) 2:1:1 | | 80 + 40 + 40 | 86 | 74 | 12 |
| (I-d) + (B.8) + (C.4) 2:0.5:1 | | 80 + 20 + 40 | 71 | 39 | 32 |

*found = activity found
**calc. = activity calculated using Colby's formula
***diff. = difference between activity found and activity calculated

Example D: In Vivo Preventive Test on *Phakopsora* Test (Soybeans)

| Solvent: | 24.5 | parts by weight of acetone |
|---|---|---|
|  | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%. The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE D1 in vivo preventive test on *Phakopsora* test (soybeans)

|  | Active compounds | Application rate of active compound in ppm a.i. | Efficacy in % | | |
|---|---|---|---|---|---|
|  |  |  | found* | calc.** | diff.*** |
| (I-d) | N'-(2,5-dimethyl-4-phenoxyphenyl)-N-ethyl-N-methylimidoformamide | 0.2 | 86 | | |
|  |  | 0.1 | 23 | | |
|  |  | 0.05 | 0 | | |
| (A.4) | tebuconazole | 0.2 | 30 | | |
|  |  | 0.1 | 0 | | |
| (B.1) | bixafen | 10 | 0 | | |
| (B.8) | N-(5-chloro-2-isopropylbenzyl)-N-cyclopropyl-3-(difluoromethyl)-5-fluoro-1-methyl-1H-pyrazole-4-carboxamide | 20 | 0 | | |
| (I-d) + (A.4) + (B.1) 1:1:100 | | 0.1 + 0.1 + 10 | 73 | 23 | 50 |
| (I-d) + (A.4) + (B.1) 1:2:200 | | 0.05 + 0.1 + 10 | 60 | 0 | 60 |
| (I-d) + (A.4) + (B.8) 1:1:100 | | 0.2 + 0.2 + 20 | 99 | 90 | 9 |
| (I-d) + (A.4) + (B.8) 1:2:200 | | 0.1 + 0.2 + 20 | 84 | 46 | 38 |

*found = activity found
**calc. = activity calculated using Colby's formula
***diff. = difference between activity found and activity calculated

TABLE D2 in vivo preventive test on *Phakopsora* test (soybeans)

| | Active compounds | Application rate of active compound in ppm a.i. | Efficacy in % found* | calc. | diff.* |
|---|---|---|---|---|---|
| (I-d) | N'-(2,5-dimethyl-4-phenoxyphenyl)-N-ethyl-N-methylimidoformamide | 0.2 | 23 | | |
| | | 0.1 | 0 | | |
| | | 0.05 | 0 | | |
| (B.6) | benzovindiflupyr | 1 | 15 | | |
| | | 0.5 | 8 | | |
| | | 0.25 | 8 | | |
| (C.1) | azoxystrobin | 1 | 68 | | |
| | | 0.5 | 20 | | |
| (C.2) | picoxystrobin | 2 | 30 | | |
| (I-d) + (B.6) + (C.1) 1:5:10 | | 0.1 + 0.5 + 1 | 94 | 71 | 23 |
| (I-d) + (B.6) + (C.1) 1:5:10 | | 0.05 + 0.25 + 0.5 | 78 | 26 | 52 |
| (I-d) + (B.6) + (C.2) 1:5:10 | | 0.2 + 1 + 2 | 83 | 54 | 29 |

*found = activity found
**calc. = activity calculated using Colby's formula
***diff. = difference between activity found and activity calculated

TABLE D3 in vivo preventive test on *Phakopsora* test (soybeans)

| | Active compounds | Application rate of active compound in ppm a.i. | Efficacy in % found* | calc. | diff.* |
|---|---|---|---|---|---|
| (I-d) | N'-(2,5-dimethyl-4-phenoxyphenyl)-N-ethyl-N-methylimidoformamide | 0.1 | 0 | | |
| | | 0.05 | 0 | | |
| (A.3) | prothioconazole | 2 | 35 | | |
| | | 1 | 0 | | |
| (B.1) | bixafen | 10 | 0 | | |
| (B.8) | N-(5-chloro-2-isopropylbenzyl)-N-cyclopropyl-3-(difluoromethyl)-5-fluoro-1-methyl-1H-pyrazole-4-carboxamide | 10 | 0 | | |
| (C.1) | azoxystrobin | 0.5 | 23 | | |
| (C.4) | trifloxystrobin | 2 | 0 | | |
| (I-d) + (A.3) + (B.1) 1:20:100 | | 0.1 + 2 + 10 | 65 | 35 | 30 |
| (I-d) + (A.3) + (B.8) 1:20:100 | | 0.1 + 2 + 10 | 80 | 35 | 45 |
| (I-d) + (A.3) + (C.1) 1:20:10 | | 0.05 + 1 + 0.5 | 78 | 23 | 55 |
| (I-d) + (A.3) + (C.4) 1:20:20 | | 0.1 + 2 + 2 | 58 | 35 | 23 |

*found = activity found
**calc. = activity calculated using Colby's formula
***diff. = difference between activity found and activity calculated Example E: In Vivo Preventive *Puccinia triticina* Test (Wheat)

| Solvent: | 49 | parts by weight of N,N-dimethylacetamide |
|---|---|---|
| Emulsifier: | 1 | part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are sprayed with a spore suspension of *Puccinia triticina*. The plants remain for 48 hours in an incubation cabinet at approximately 20° C. and a relative atmospheric humidity of approximately 100%. The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE E1 in vivo preventive *Puccinia triticina* test (wheat)

| | Active compounds | Application rate of active compound in ppm a.i. | Efficacy in % | | |
|---|---|---|---|---|---|
| | | | found* | calc.** | diff.*** |
| (I-d) | N'-(2,5-dimethyl-4-phenoxyphenyl)-N-ethyl-N-methylimidoformamide | 40 | 57 | | |
| (B.6) | benzovindiflupyr | 40 | 86 | | |
| (C.1) | azoxystrobin | 10 | 71 | | |
| (I-d) + (B.6) + (C.1) 4:4:1 | | 40 + 40 + 10 | 100 | 98 | 2 |

*found = activity found
**calc. = activity calculated using Colby's formula
***diff. = difference between activity found and activity calculated

Example F: In Vivo Preventive *Pyrenophora teres* Test (Barley)

| Solvent: | 49 | parts by weight of N,N-dimethylacetamide |
|---|---|---|
| Emulsifier: | 1 | part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are sprayed with a spore suspension of *Pyrenophora teres*. The plants remain for 48 hours in an incubation cabinet at approximately 20° C. and a relative atmospheric humidity of approximately 100%. The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

Example G: In Vivo Preventive *Septoria tritici* Test (Wheat)

| Solvent: | 49 | parts by weight of N,N-dimethylacetamide |
|---|---|---|
| Emulsifier: | 1 | part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%. The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE F1 in vivo preventive *Pyrenophora teres* test (barley)

| | Active compounds | Application rate of active compound in ppm a.i. | Efficacy in % | | |
|---|---|---|---|---|---|
| | | | found* | calc.** | diff.*** |
| (I-d) | N'-(2,5-dimethyl-4-phenoxyphenyl)-N-ethyl-N-methylimidoformamide | 80 | 29 | | |
| (B.6) | benzovindiflupyr | 80 | 57 | | |
| (C.1) | azoxystrobin | 20 | 71 | | |
| (I-d) + (B.6) + (C.1) 4:4:1 | | 80 + 80 + 20 | 100 | 91 | 9 |

*found = activity found
**calc. = activity calculated using Colby's formula
***diff. = difference between activity found and activity calculated

TABLE G1 in vivo preventive *Septoria tritici* test (wheat)

| | Active compounds | Application rate of active compound in ppm a.i. | Efficacy in % found* | calc. | diff.* |
|---|---|---|---|---|---|
| (I-d) | N'-(2,5-dimethyl-4-phenoxyphenyl)-N-ethyl-N-methylimidoformamide | 40 | 14 | | |
| | | 20 | 14 | | |
| (A.3) | prothioconazole | 20 | 0 | | |
| (B.8) | N-(5-chloro-2-isopropylbenzyl)-N-cyclopropyl-3-(difluoromethyl)-5-fluoro-1-methyl-1H-pyrazole-4-carboxamide | 20 | 29 | | |
| (I-d) + (A.3) + (B.8) 2:1:1 | | 40 + 20 + 20 | 57 | 39 | 18 |
| (I-d) + (A.3) + (B.8) 1:1:1 | | 20 + 20 + 20 | 43 | 39 | 4 |

*found = activity found
**calc. = activity calculated using Colby's formula
***diff. = difference between activity found and activity calculated

TABLE G2 in vivo preventive *Septoria tritici* test (wheat)

| | Active compounds | Application rate of active compound in ppm a.i. | Efficacy in % found* | calc. | diff.* |
|---|---|---|---|---|---|
| (I-d) | N'-(2,5-dimethyl-4-phenoxyphenyl)-N-ethyl-N-methylimidoformamide | 80 | 0 | | |
| | | 40 | 0 | | |
| (B.1) | bixafen | 40 | 0 | | |
| (B.3) | fluxapyroxad | 40 | 13 | | |
| (B.6) | benzovindiflupyr | 40 | 38 | | |
| (C.1) | azoxystrobin | 10 | 0 | | |
| (C.3) | pyraclostrobin | 40 | 88 | | |
| (C.4) | trifloxystrobin | 20 | 75 | | |
| (I-d) + (B.1) + (C.4) 2:1:1 | | 40 + 40 + 20 | 94 | 75 | 19 |
| (I-d) + (B.3) + (C.3) 2:1:1 | | 80 + 40 + 40 | 94 | 90 | 4 |
| (I-d) + (B.6) + (C.1) 4:4:1 | | 40 + 40 + 10 | 50 | 38 | 12 |

*found = activity found
**calc. = activity calculated using Colby's formula
***diff. = difference between activity found and activity calculated

The invention claimed is:

1. An active compound combination comprising
(1) at least one compound of the formula (I)

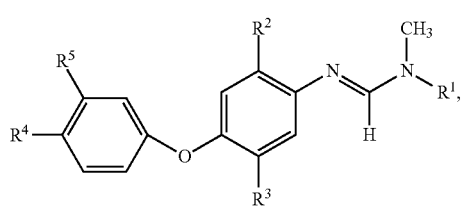

in which
R$^1$ is selected from the group consisting of methyl and ethyl;
R$^2$ is selected from the group consisting of a Cl atom and a methyl group;
R$^3$ is selected from the group consisting of a Cl-atom and a methyl group;
R$^4$ is selected from the group consisting of hydrogen, halogen or methyl;
R$^5$ is selected from the group consisting of hydrogen, halogen or methyl;

and/or a salt, N-oxide, metal complex and/or stereoisomer thereof and
(2) at least two compounds (II) and (III) selected from the groups (A), (B) and/or (C):
(A) the group of inhibitors of the ergosterol biosynthesis;
(B) the group of inhibitors of the respiratory chain at complex I or II; and
(C) the group of inhibitors of the respiratory chain at complex III;
with the proviso that the specified compounds (II) and (III) are not identical,
and wherein the compound of the group (A) of inhibitors of the ergosterol biosynthesis is selected from the group consisting of (A.1) cyproconazole (113096-99-4), (A.2) epoxiconazole (106325-08-0), (A.3) prothioconazole (178928-70-6) and (A.4) tebuconazole (107534-96-3);
and wherein the compound of the group (B) of inhibitors of the respiratory chain at complex I or II is selected from the group consisting of (B.1) bixafen (581809-46-3), (B.2) fluopyram (658066-35-4), (B.3) fluxapyroxad (907204-31-3), (B.4) isopyrazam (mixture of syn-epimeric racemate 1RS,4SR,9RS and anti-epimeric racemate 1RS,4SR,9SR) (881685-58-1), (B.5)

penthiopyrad (183675-82-3), (B.6) benzovindiflupyr (1072957-71-1), (B.7) isofetamid (875915-78-9), (B.8) N-(5-chloro-2-isopropylbenzyl)-N-cyclopropyl-3-(difluoromethyl)-5-fluoro-1-methyl-1H-pyrazole-4-carboxamide and (B.9) 3-(difluoromethyl)-N-methoxy-1-methyl-N-[1-(2,4,6-trichlorophenyl)propan-2-yl]-1H-pyrazole-4-carboxamide, and wherein the compound of the group (C) of inhibitors of the respiratory chain at complex III is selected from the group consisting of (C.1) azoxystrobin (131860-33-8), (C.2) picoxystrobin (117428-22-5), (C.3) pyraclostrobin (175013-18-0) and (C.4) trifloxystrobin (141517-21-7).

2. An active compound combination according to claim 1, wherein the compound of formula (I) is represented by a compound according to formula (I-d):

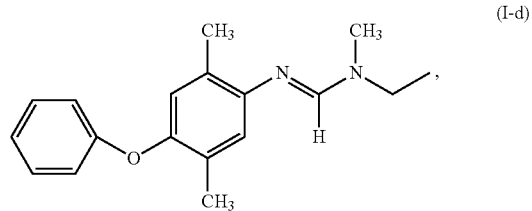 [SMILES: CCN(C)/C=N/c1cc(C)c(Oc2ccccc2)cc1C]

and/or a salt, N-oxide, metal complex and/or stereoisomer thereof.

3. The active compound combination according to claim 2, selected from the group consisting of (I-d)+benzovindiflupyr+tebuconazole; (I-d)+benzovindiflupyr+cyproconazole; (I-d)+benzovindiflupyr+epoxiconazole; (I-d)+penthiopyrad+cyproconazole; (I-d)+penthiopyrad+epoxiconazole; (I-d)+fluxapyroxad+prothioconazole; (I-d)+fluxapyroxad+tebuconazole; (I-d)+fluxapyroxad+epoxiconazole; (I-d)+isopyrazam+cyproconazole; (I-d)+isopyrazam+epoxiconazole; (I-d)+trifloxystrobin+Benzovindiflupyr; (I-d)+trifloxystrobin+fluxapyroxad; (I-d)+azoxystrobin+tebuconazole; (I-d)+azoxystrobin+cyproconazole; (I-d)+azoxystrobin+epoxiconazole; (I-d)+azoxystrobin+bixafen; (I-d)+azoxystrobin+fluxapyroxad; (I-d)+azoxystrobin+isopyrazam; (I-d)+pyraclostrobin+prothioconazole; (I-d)+pyraclostrobin+tebuconazole; (I-d)+pyraclostrobin+epoxiconazole; (I-d)+pyraclostrobin+bixafen; (I-d)+picoxystrobin+prothioconazole; (I-d)+Picoxystrobin+tebuconazole; (I-d)+N-(5-chloro-2-isopropylbenzyl)-N-cyclopropyl-3-(difluoromethyl)-5-fluoro-1-methyl-1H-pyrazole-4-carboxamide+azoxystrobin; (I-d)+N-(5-chloro-2-isopropylbenzyl)-N-cyclopropyl-3-(difluoromethyl)-5-fluoro-1-methyl-1H-pyrazole-4-carboxamide+pyraclostrobin; (I-d)+3-(difluoromethyl)-N-methoxy-1-methyl-N-[1-(2,4,6-trichlorophenyl)propan-2-yl]-1H-pyrazole-4-carboxamide+tebuconazole; (I-d)+3-(difluoromethyl)-N-methoxy-1-methyl-N-[1-(2,4,6-trichlorophenyl)propan-2-yl]-1H-pyrazole-4-carboxamide+bixafen and (I-d)+3-(difluoromethyl)-N-methoxy-1-methyl-N-[1-(2,4,6-trichlorophenyl)propan-2-yl]-1H-pyrazole-4-carboxamide+benzovindiflupyr.

4. The active compound combination according to claim 2, selected from the group consisting of (I-d)+fluopyram+tebuconazole; (I-d)+trifloxystrobin+cyproconazole; (I-d)+isofetamid+prothioconazole; (I-d)+isofetamid+tebuconazole; (I-d)+fluopyram+bixafen; (I-d)+trifloxystrobin+fluopyram; (I-d)+isofetamid+bixafen and (I-d)+isofetamid+trifloxystrobin.

5. The active compound combination according to claim 2, selected from the group consisting of (I-d)+bixafen+prothioconazole; (I-d)+fluopyram+prothioconazole; (I-d)+benzovindiflupyr+prothioconazole; (I-d)+trifloxystrobin+prothioconazole; (I-d)+azoxystrobin+prothioconazole; (I-d)+N-(5-chloro-2-isopropylbenzyl)-N-cyclopropyl-3-(difluoromethyl)-5-fluoro-1-methyl-1H-pyrazole-4-carboxamide+prothioconazole; (I-d)+bixafen+tebuconazole; (I-d)+trifloxystrobin+tebuconazole; (I-d)+N-(5-chloro-2-isopropylbenzyl)-N-cyclopropyl-3-(difluoromethyl)-5-fluoro-1-methyl-1H-pyrazole-4-carboxamide+tebuconazole; (I-d)+trifloxystrobin+bixafen; (I-d)+azoxystrobin+benzovindiflupyr; (I-d)+picoxystrobin+penthiopyrad; (I-d)+picoxystrobin+benzovindiflupyr; (I-d)+pyraclostrobin+fluxapyroxad and (I-d)+N-(5-chloro-2-isopropylbenzyl)-N-cyclopropyl-3-(difluoromethyl)-5-fluoro-1-methyl-1H-pyrazole-4-carboxamide+trifloxystrobin.

6. A composition comprising an active compound combination according to claim 1.

7. A composition according to claim 6 further comprising at least one agriculturally suitable additive.

8. A method for preparing a composition according to claim 6 comprising adding at least one agriculturally suitable additive to the active compound combination according to claim 1.

9. A method for reducing damage of plants and plant parts or losses in harvested fruits or vegetables caused by phytopathogenic fungi by controlling such phytopathogenic fungi, comprising applying the active compound combination according to claim 1 to the plant or the phytopathogenic fungi or the habitat of the plant or the habitat of the phytopathogenic fungi.

10. A method for curatively or preventively controlling phytopathogenic fungi comprising application of an active compound combination according to claim 1 or a composition thereof for control of one or more soybean diseases.

11. A method for curatively or preventively controlling phytopathogenic fungi comprising application of an active compound combination according to claim 1 or a composition thereof for control of one or more cereal diseases.

12. Seed treated with the active compound combination according to claim 1 or a composition thereof, wherein the treatment comprises-contacting said seed with the active compound combination.

13. The method according to claim 9, wherein the plants are genetically modified.

14. The active compound combination according to claim 1, comprising a compound of formula (I) and a compound (II) in a weight ratio of 1:1 to 1:20.

15. The active compound combination according to claim 1, comprising a compound of formula (I) and a compound (III) in a weight ratio of 1:1 to 1:10.

16. The active compound combination according to claim 14, comprising a compound of formula (I) and a compound (III) in a weight ratio of 1:1 to 1:10.

17. The active compound combination according to claim 1, comprising tebuconazole.

18. The active compound combination according to claim 1, comprising prothioconazole.

* * * * *